(12) United States Patent
Pantsar et al.

(10) Patent No.: US 8,532,254 B2
(45) Date of Patent: *Sep. 10, 2013

(54) EXTRA-ORAL DIGITAL PANORAMIC DENTAL X-RAY IMAGING SYSTEM

(75) Inventors: Tuomas Pantsar, Espoo (FI); Konstantinos Spartiotis, Espoo (FI)

(73) Assignee: Oy AJAT Ltd, Espoo (FI)

( * ) Notice: Subject to any disclaimer, the term of this patent is extended or adjusted under 35 U.S.C. 154(b) by 115 days.

This patent is subject to a terminal disclaimer.

(21) Appl. No.: 12/769,102

(22) Filed: Apr. 28, 2010

(65) Prior Publication Data

US 2010/0246761 A1  Sep. 30, 2010

Related U.S. Application Data

(63) Continuation of application No. 12/613,558, filed on Nov. 6, 2009, which is a continuation of application No. 11/673,583, filed on Feb. 11, 2007, now Pat. No. 7,676,022, which is a continuation-in-part of application No. 11/277,530, filed on Mar. 27, 2006, now Pat. No. 7,336,763.

(60) Provisional application No. 60/677,020, filed on May 2, 2005.

(51) Int. Cl.
  *A61B 6/14* (2006.01)
  *H05G 1/02* (2006.01)
  *H05G 1/60* (2006.01)

(52) U.S. Cl.
  USPC .................................. 378/38; 378/39; 378/40

(58) Field of Classification Search
  USPC ............................ 378/4–20, 38–40, 193, 197
  See application file for complete search history.

(56) References Cited

U.S. PATENT DOCUMENTS

| | | | |
|---|---|---|---|
| 4,188,537 A | 2/1980 | Franke | |
| 4,239,971 A | 12/1980 | Cushman | |
| 4,823,369 A | 4/1989 | Guenther et al. | |
| 4,878,234 A | 10/1989 | Pfeiffer et al. | |
| 4,956,556 A | 9/1990 | Radtke | |
| 4,995,062 A | 2/1991 | Schulze-Ganzlin et al. | |
| 5,195,114 A | 3/1993 | Sairenji et al. | |

(Continued)

FOREIGN PATENT DOCUMENTS

| | | |
|---|---|---|
| EP | 0 673 623 | 9/1995 |
| EP | 0776124 A2 | 5/1997 |

(Continued)

OTHER PUBLICATIONS

Yaniv et al., Long Bone Panoramas From Fluoroscopic X-Ray Images, IEEE Transactions on medical imaging, vol. 23, No. 1, Jan. 2004.

(Continued)

*Primary Examiner* — Anastasia Midkiff
(74) *Attorney, Agent, or Firm* — Young & Thompson

(57) ABSTRACT

An extra-oral digital panoramic dental x-ray imaging system for multi-layer panoramic and transverse X-ray imaging providing with an X-ray source and a digital imaging device providing real time frame mode output and autofocusing. The X-ray source and imaging device are mounted in a mechanical manipulator defining the trajectory of a predetermined image layer. The imaging device communicates with a processor that generates a frames memory from which an image reconstruction mechanism composes the final images.

15 Claims, 11 Drawing Sheets

(56) References Cited

U.S. PATENT DOCUMENTS

| | | | |
|---|---|---|---|
| 5,214,686 A | 5/1993 | Webber | |
| 5,528,043 A | 6/1996 | Spivey et al. | |
| 5,677,940 A | 10/1997 | Suzuki et al. | |
| 5,744,806 A | 4/1998 | Frojd | |
| 5,784,429 A * | 7/1998 | Arai | 378/38 |
| 5,828,721 A | 10/1998 | Schulze-Ganzlin et al. | |
| 5,848,123 A | 12/1998 | Strommer | |
| 6,009,142 A | 12/1999 | Sauer et al. | |
| 6,049,584 A | 4/2000 | Pfeiffer | |
| 6,493,415 B1 * | 12/2002 | Arai et al. | 378/4 |
| 6,496,557 B2 | 12/2002 | Wilson et al. | |
| 6,741,251 B2 | 5/2004 | Malzbender | |
| 7,016,461 B2 | 3/2006 | Rotondo et al. | |
| 7,136,452 B2 | 11/2006 | Spartiotis et al. | |
| 7,336,763 B2 * | 2/2008 | Spartiotis et al. | 378/40 |
| 7,676,022 B2 * | 3/2010 | Pantsar et al. | 378/39 |
| 7,798,708 B2 | 9/2010 | Erhardt et al. | |
| 2003/0034977 A1 | 2/2003 | Malzbender | |
| 2003/0058989 A1 * | 3/2003 | Rotondo et al. | 378/40 |
| 2003/0215051 A1 * | 11/2003 | Suzuki | 378/19 |
| 2004/0000630 A1 * | 1/2004 | Spartiotis et al. | 250/208.1 |
| 2004/0190678 A1 * | 9/2004 | Rotondo et al. | 378/38 |
| 2009/0022270 A1 * | 1/2009 | Yoshimura et al. | 378/19 |

FOREIGN PATENT DOCUMENTS

| | | |
|---|---|---|
| EP | 1520300 | 9/2003 |
| JP | 6078919 A | 3/1994 |
| JP | 7308314 A | 11/1995 |
| JP | 2000217810 A | 8/2000 |
| JP | 2004536643 A | 12/2004 |
| WO | 02052505 A2 | 7/2002 |
| WO | WO 02/052505 | 7/2002 |
| WO | WO 2004/055550 | 7/2004 |
| WO | 2004084728 A1 | 10/2004 |

OTHER PUBLICATIONS

Dobbins et al., "Digital x-ray tomosynthesis: current state of the art and clinical potential", Institute of Physics Publishing, Phys. Med. Biol. 48 (2003) R65-R106.

Lee et al., "A 3-D X-Ray Microtomographic System With a CMOS Image Sensor", IEEE Transactions on Nuclear Science, vol. 48, No. 4, Aug. 2001, p. 1503-1505.

Ruttimann et al., "Computer Tomosynthesis: A Versatile Three-Dimensional Imaging Technique", National Institute of Dental Research, National Institutes of Health, MD, USA, p. 783-786.

Williams et al., "Evaluation of a Prototype Detector for Full Breast Digital Mammography with CCDs and Modified Schmidt Camera Optics", RSNA, 1997, p. 1-14.

* cited by examiner

EXTRA-ORAL DIGITAL PANORAMIC DENTAL X-RAY IMAGING SYSTEM

CROSS REFERENCE TO RELATED APPLICATIONS

The present application is a continuation of U.S. application Ser. No. 12/613,558 filed Nov. 6, 2009, which is a continuation of U.S. patent application Ser. No. 11/673,583 filed Feb. 11, 2007, which was a continuation-in-part of U.S. patent application Ser. No. 11/277,530 filed Mar. 27, 2006, which claimed the benefit of prior filed U.S. Provisional Application Ser. No. 60/677,020 filed May 2, 2005.

FIELD OF THE INVENTION

The present invention is in the field of apparatuses and corresponding processes involving the use of radiation within the X-ray spectrum with specific features characteristic of X-ray applications. More specifically, the present invention relates to digital dental panoramic imaging apparatuses producing a digital image of a curved dental structure, wherein a digital image of all teeth on upper and/or lower jaws is formed in a single digital image.

BACKGROUND OF THE INVENTION

Dental panoramic X-ray imaging is a well-known dental radiographic procedure. Its purpose is to produce an X-ray image of the entire jaw for diagnosis as opposed to a partial image such as obtained by intra-oral X-ray imaging. Other extra-oral dental X-ray imaging systems include cone beam dental computed tomography (CT) system for 3-D tomosynthetic volumetric reconstruction and transverse slicing. Regular panoramic imaging is used mostly from general purpose orthodontics, while 3-D imaging and transverse slicing maybe used more often for dental implantation.

Dental panoramic X-ray imaging units, cone beam units and transverse slicing units, a.k.a. orthopantomographs (OPGs) or dental CT's, are available with analog film were suitable and with digital sensors (in case of cone beam CT). Digital OPGs currently available in the market utilize sensors based on CCDs coupled to a phosphor or scintillator, and operate in a Time Delay Integration Mode (TDI), or flat panels utilizing a-Si (amorphous silicon) TFT arrays (Thin Film Transistor) with again a scintillator on the top. Both CCD's and TFT flat panels used convert x-rays to light and then light is converted to an electronic signal inside the CCD or TFT. This equipment and especially the cone beam CT and transverse slicing equipment which produce multiple frames, these systems are not fast enough for continuous exposure. Consequently, real time viewing is not possible. A fully equipped dental office needs to have several types of so called "intra-oral" sensors to complete the range of functionalities needed to cover general maxillofacial examinations, fillings and cavities, orthodontics, implantology and surgery. As can be appreciated, this is a cost burden that probably only large clinics can afford.

An orthopantomograph is made up of four functional units: an X-ray generator; an imaging device; a mechanical manipulator; and a user control panel. The purpose of the X-ray generator is to create the x-rays that penetrate the head of the patient and arrive at the imaging device. The X-ray generator or source is able to generate x-rays with different spectra by varying the high voltage level and with differing intensity by varying the current. The imaging device detects and converts the x-rays incident on it into an image. The mechanical manipulator displaces both the imaging device and the X-ray generator in such a way that a proper panoramic image of the plane-of-interest is formed. The user control panel or the user interface, is used to control different settings of the OPG or to initiate and control an X-ray exposure event.

Currently digital imaging devices accomplish their purpose through: absorption by traditional films, or by digital two-stage indirect conversion (using a CCD with a scintillator). Linear arrays of CCD's are used in OPG's but flat panels based on TFT or image intensifiers are used in cone beam dental CT. A typical cone beam dental CT system does not differ in any substantial way from the OPG system, except that the X-ray beam is cone shaped rather than fan shaped. Additionally the cone beam systems require that the X-ray scan be performed for longer times and in step fashion (i.e., not continuously) because Image Intesifiers (IIs) or TFT panels are too slow and lack sensitivity.

Dental Panoramic, Dental Transverse and Dental 3-D X-Ray Imaging

In dental panoramic X-ray imaging, the image is captured during a process in which both the X-ray generator and the imaging device move around the patient's head according to a predetermined geometric path and speed profile. The movement is synchronized in such a way that an image of the pre-determined layer of interest is formed according to the predetermined geometry and speed profile. Because of the shape of the human jaw, this layer is a non-planar structure. It in fact varies with the morphology of each individual's jaw. To simplify the procedure while still maintaining high resolution, a standard shape is used that is applied to all human males, females, and children of certain ages, is used. The exact shape of the layer-of-interest depends on the dental procedure in question; the predetermined geometric path of the source and detector (optionally varying depending on the patient type); and the predetermined speed profile. The layer can usually be adjusted by selecting a different pre-determined, preset program in the OPG by changing the path of movement and/or also the speed profile. Different programs can alter the general parameters of the profile to match the patient (again, e.g., whether child or adult) or to only image a part of the full profile (i.e., front teeth, left/right side etc.). But in each case when a new panoramic layer is needed a new exposure needs to be taken, which means additional radiation to the patient.

The movement of the X-ray generator and the imaging device is traditionally synchronized so that the imaging device surface normal is perpendicular to the layer-of-interest. In this way the formed image is distorted as little as possible. A disadvantage of this approach is that the movement trajectory is quite complex. To achieve this motion, multiple motors are required (i.e. degrees of freedom) which also complicates the control electronics and algorithms, thus leading to higher cost. There are some imaging modalities in which the direction of radiation is intentionally not perpendicular to the surface normal, but the same drawbacks and advantages apply. In addition, one of the most severe issues experienced today in clinical applications of dental panoramic imaging is that the patient (object) does or cannot necessarily remain motionless for the whole duration of the scan (typically lasting 5 to 30 seconds). Even a small misalignment of the patient can result in that the part of the imaged layer being blurred or out of focus. In addition to panoramic images, a dentist may wish to create a transverse slice image of the patient's jaw. In transverse imaging, the layer-of-interest is perpendicular to the panoramic layer.

The existing commercially available, extra-oral (including, for example, panoramic and transverse) imaging solutions are either based on elongated (i.e., with an aspect ratio—length "m" divided by width "n"—of m/n=5 or more) time-delayed integration CCD sensors (not producing multiple frames) or on large-area 2D detectors with a computed tomography system backend where m/n is substantially equal to 1 (which, however, do produce multiple frames). The large-area 2D detectors are most often TFT panels and are particularly expensive because of the m/n.apprxeq.1 aspect ratio (approximately equal to one). The elongated detectors, which use a CCD coupled with a scintillator, apply the time-delayed integration (TDI) principle to form the image of the layer of interest. Time-Delay Integration is a method of synchronizing the shifting of the image signal captured in the pixel with the movement of the object image across the face of the CCD. This permits integration of more signal, increasing sensitivity, reducing noise and reducing image blur. According to this method, the integrated charges are clocked inside the detector logic (CCD) in the direction of the movement. Thus, at a given integration period $t_i$, the charge for a fixed object volume v is integrated to a pixel $p_n$. The object is moved so that the image of the plane-of-interest is moved (taking the magnification factor into account) exactly a pixel's width. After the integration period, the charges are transferred in such a way that if the image of the volume v is projected to pixel $p_{i-1}$, the charged from pixel $p_i$ is transferred to pixel $p_{i-1}$. The last pixel value in the row, which has no neighbor to which to transfer the charge, is read out and stored in the final image. In this way, the apparent integration time of an image pixel is the integration period multiplied by the width of the imaging device in pixels.

With the TDI principle, the clocking of the charges must be synchronized so that the apparent speed of the layer-of-interest in the imaging devices active in an integration period must be exactly the width of the pixel. If the speed is not matched, the image will appear blurred. A 2D flat image is formed from a single scan using an imaging device operating in the TDI mode. Multiple panoramic layers, transverse slicing or 3D imaging is not possible because only a single projection is saved.

In a dental cone beam computed tomography system (3-D imaging), multiple, non-TDI exposures are taken with a 2D area detector where m substantially equals n (i.e. within 20%). The movement is stopped before the exposure and the X-ray source is only active during this stationary period. The movement is continued after the exposure. In this manner, the movement doesn't have to be synchronized. Such systems require a higher dose to be administered to the patient and also longer examination times. The final image is formed as a layer calculated from the volumetric (3D) dataset constructed from the individual exposures or projections. The clear advantage of this method is that a full 3D volumetric dataset will be available after the procedure. However, with current solutions, the resolution of panoramic layer calculated from the 3D data is low compared to dedicated panoramic imaging systems (OPGs). Furthermore, the dose levels are much higher and maybe equally importantly the cost of such available systems is in the range of 200 kUSD-400 kUSD.

U.S. Pat. No. 6,496,557, entitled "Two Dimensional Slot X-ray Bone Densitometry, Radiography and Tomography," describes a process in which multiple layers are formed by a so-called shift-and-add algorithm. The process described includes a system in which the motion of the imaging device is either linear or includes a rotational component around the focal point of the X-ray source. Unfortunately, such a system cannot be used in the field of dental X-ray imaging where the layer(s) of Interest run around or across the human jaw. Although such an approach may be useful in bone densitometry and in some other applications, it is in practice impossible to apply to dental panoramic or transverse imaging due to the fact that x-rays run essentially parallel to rather than across the layer-of-interest, should there be linear movement or rotation around the focal point. Additionally, the process disclosed in U.S. Pat. No. 6,496,557 would have another serious limitation if an attempt were to be made to apply it in the field of dental imaging. That limitation is the most serious issue in panoramic imaging and it results in partial image blurring due to misalignment of the patient or due to patient movement. Also, U.S. Pat. No. 6,496,557 fails to address the need of a system or a procedure that is able to simultaneously perform both panoramic as well as transverse imaging. Further, this patent fails to disclose a system operable in a dental imaging environment.

U.S. Pat. No. 5,784,429, entitled "Dental panoramic X-ray imaging apparatus," describes a system in which multiple layers are calculated using plural tomographic images corresponding to plural tomographic planes which are arranged at predetermined intervals along the direction of the X-ray irradiation. A convolution process or a frequency process is conducted on a specific tomographic image by using image information of at least one of the tomographic images, so as to remove blur from the specific tomographic image. This patent describes a means of implementing different layers by using image intensifiers, CCD's or combinations thereof.

U.S. Pat. No. 7,136,452, entitled "Radiation Imaging System and Scanning Device," discloses the use of frame mode CdTe-CMOS detectors for creating tomographic images in several applications including dental panoramic images using a dental X-ray setup. In U.S. Pat. No. 7,136,452, Spartiotis et al. disclose that the read-out speed or frame rate must be high enough to allow the detector to move by no more than half a pixel size or preferably even less per a read-out cycle. Emphasis added. However, if a system is implemented in such a way, serious limitations can arise such as the need to transfer a disproportionately large amount of data to a computer or the like in real-time. However, '452 patent is silent on the management of data to reconstruct and display an image in real-time, during the exposure. Furthermore, Spartiotis et al. teach nothing about one of the most serious issues facing dental radiology, that of partial image blurring due to patient misalignment and how to create automatically a focused layer. In such cases, part of the image (i.e., the panoramic layer-of-interest) is blurred while another part is in focus. Spartiotis et al. merely disclose that the frame rate needs be very high to collect frames in such a case in which the detector has moved by less than half a pixel, but does not teach how to accomplish this. Unfortunately, in this case, the amount of data produced during the exposure is unnecessarily high while at the same time, no material performance benefit is gained. Additionally, Spartiotis et al. do not suggest a means by which one might combine data to gain performance benefits and to correct blurring or to produce transverse image slices or even tomosynthentic 3D images.

Devices exist that are capable for example of performing transverse slicing or 3-D reconstructed images, but most often they require much longer X-ray scan times and non-continuous scan (i.e., a step by step scan). The long exposures are needed because the normally used digital imaging devices lack sensitivity and typically can "catch" only 1 out of 3 incoming x-rays. Further, non-continuous step-wise scans are necessary in the prior art because of the slow response and slow readout of the current rectangular or square flat panel TFT arrays. Higher doses and longer step-wise scans create higher risk and discomfort to the patient.

Additionally, the prior art does not suggest a means by which one might combine data to gain performance benefits and to correct blurring or to produce transverse image slices or even tomosynthetic 3D images. What is needed, therefore, is a system that limits the radiation doses a patient receives while maximizing the data output. Further, what is needed is a system which permits continuous fast, real-time X-ray scans, and a system and method of combining data from a single exposure to, not only reconstruct a panoramic layer of interest, but to also be able to correct part of the image that is blurred and furthermore produce transverse image slices and 3D images. Still further needed is a system that is capable of correcting blurring and which can produce transverse image slices or tomosynthetic 3D image.

SUMMARY OF THE INVENTION

The present invention is an extra-oral dental X-ray digital imaging system. The present system produces digital panoramic extra-oral dental X-ray images, including multi-layer dental panoramic and transverse X-ray images. The system includes an X-ray source, a digital imaging device having a frame mode output capable of a high frame rate, a mechanical manipulator having at least one rotation axis located in a position other that the focal point of the X-ray source and means of detecting the camera position in 1D, 2D or 3D depending of the complexity of the trajectory and means of reconstructing the final images out of the stored frames. Also included are a real time storage system such as RAM, a hard drive or a drive array able to store all the frames captured during an exposure, and a digital processing unit interconnected in operational arrangement with the other components and capable of executing the reconstruction algorithm. The present system is adapted to produce selectively two or more of the following: 1) a predetermined dental panoramic layer image 2) at least part of a non predetermined dental panoramic layer image 3) transverse slice to a selected part of a dental panoramic layer image 4) 3-D reconstruction of a volume corresponding to some part of a dental panoramic layer, all from image data from a single exposure.

In particular, the system combines a fast readout with a memory of comparable speed, i.e., a memory which stores and accesses information substantially in any order and in which all storage locations are substantially equally accessible. Such a memory has sufficient speed for storing the multiple frames concurrently with the exposure in a manner which permits retrieval and display in real time. Preferably such system should employ an X-ray imaging device having an aspect ratio of m/n>1.2 where m is the long dimension and n is the short dimension of the active area of the imaging device. In accomplishing its advantages, the present system causes substantially no greater radiation exposure than the dose used in a regular dental panoramic exposure, while performing the X-ray scan to collect such data in a continuous movement. Additionally, the detector device produces a variety of formats of panoramic images from a high-speed, X-ray digital imaging device. In a further advantage, the present system and method combines data from a single exposure to not only reconstruct a panoramic layer of interest but to also be able to correct part of the image that is blurred and furthermore produce transverse image slices and 3D images.

DETAILED DESCRIPTION OF THE INVENTION

Figure 1:
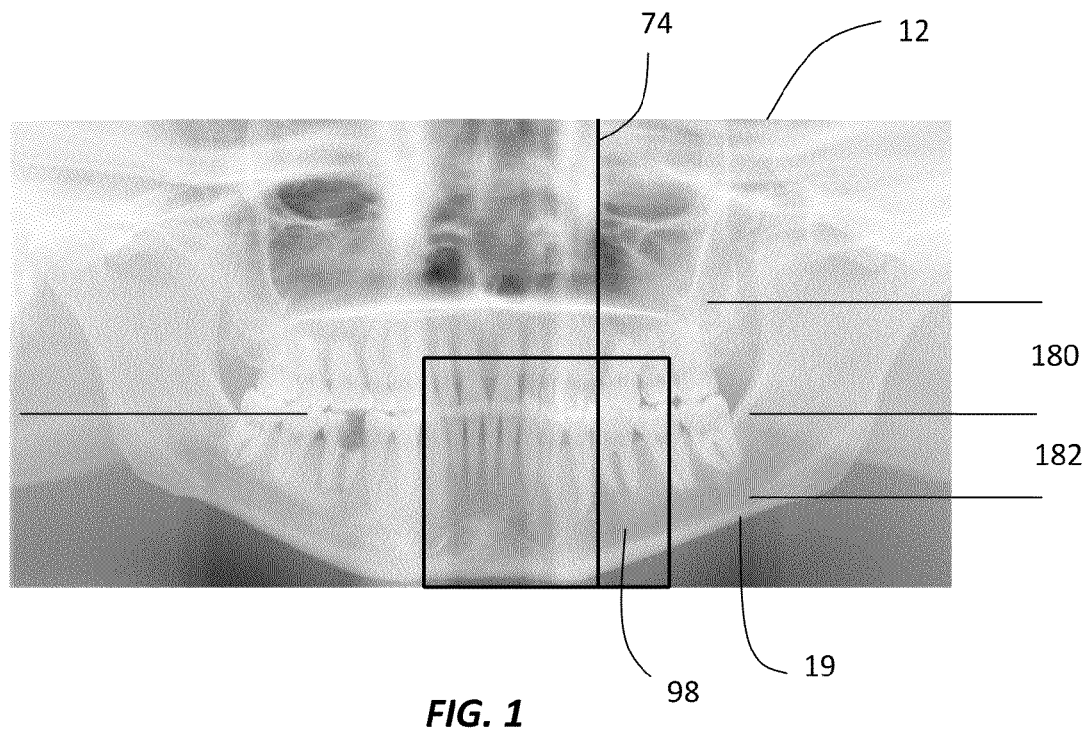
FIG. 1 is an X-ray photograph of a sample dental panoramic X-ray image produced using the present invention.

Referring now to the drawings, the details of preferred embodiments of the present invention are graphically and schematically illustrated. Like elements in the drawings are represented by like numbers, and any similar elements are represented by like numbers with a different lower case letter suffix.

Figure 2:
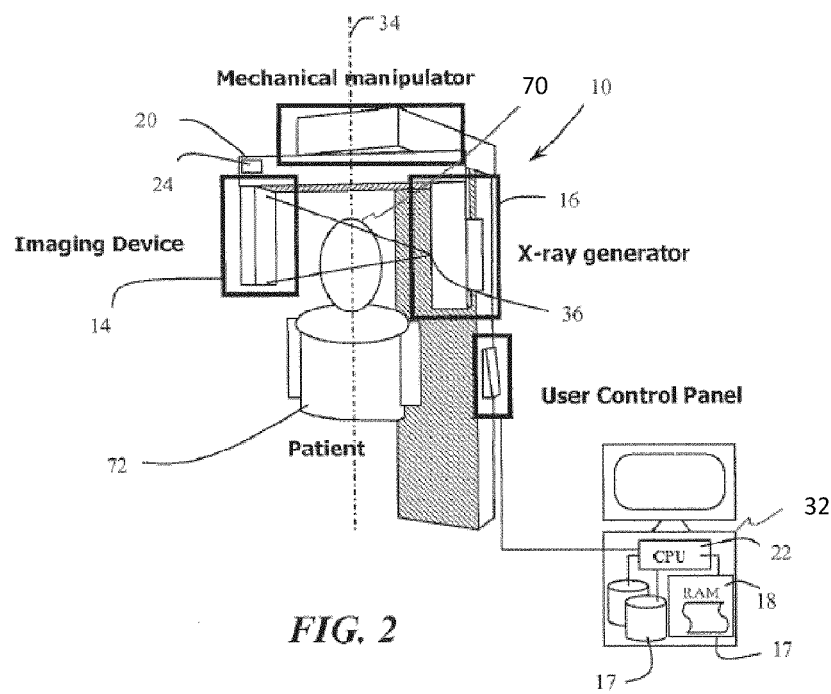
FIG. 2 is a schematic view of a dental panoramic X-ray imaging system.

Referring to FIGS. 1 and 2, the system 10 of the invention uses a frame mode CdTe-CMOS detectors for creating tomographic images including dental panoramic images using a dental X-ray setup. In this application, the read-out speed or frame rate need only be high enough to allow the detector to move by more than half a pixel size and preferably less a full pixel read-out cycle. However, serious limitations can arise such as the need to transfer a disproportionately large amount of data to a computer or the like in real-time. Therefore, it is beneficial to manage data in order to reconstruct and display an image in real-time, during the exposure.

The dental X-ray imaging system 10 produces panoramic images 12 for use in dental diagnosis and treatment. The system 10, using data generated from a single exposure, selectively produces at least two of the following: 1) a predetermined dental panoramic layer image 2) at least part of another dental panoramic layer(s) 3) transverse slice to a selected part of a dental panoramic layer image 4) 3-D reconstruction of a volume corresponding to some part of a dental panoramic layer.

The system 10 preferably employs a detector having an aspect ratio of its long m to short n dimensions in its "active area" with an m/n ratio greater than 1.5. The "active area" is the portion of the X-ray imaging device that is sensitive to detecting X-ray flux. This is advantageous because such a detector is much more economical and practical than a full square area detector. Although digital detector prices are dropping, it is still the case that a full field digital imaging device having sufficient resolution is much more expensive than an elongated imaging device. In a preferred embodiment, the present invention uses a digital imaging device having detector substrate made of a Cadmium and Telluride composition, such as CdTe or CdZnTe (Cadmium Zinc Telluride). Additionally, it is preferred that the detector is bump-bonded to a readout substrate, e.g., a Complementary Metal Oxide Semiconductor (CMOS) Application Specific Integrated Circuit (ASIC). CdTe and CdZnTe detectors bump-bonded to CMOS ASIC are preferred as suitably fast X-ray imaging devices, due to their high density and absorption efficiency, readout speed and resolution.

The dental X-ray imaging system 10 in accordance with the present invention includes an X-ray source 16 for generating the radiation to be detected by the digital imaging device 14. The digital imaging device 14 has a frame mode output with a sufficiently high frame rate as set forth below. A mechanical manipulator 20 mounts hardware of the source 16 and imaging device 14. The mechanical manipulator has at least one rotation axis located in a position other that the focal point of the X-ray source, and includes an alignment estimator 24. A reconstruction algorithm 26 (see FIGS. 8a-8c) reconstructs at least two final digital imaging device 14 images out of the same set of stored frames 40 (see FIG. 5b) from a single exposure. A storage system 17 is used to temporarily storing all the data in effectively real time, and a processing unit 22 such as a personal computer, is used to control certain processes of the system 10.

The X-ray source 16 is a radiation source such as an X-ray generator or a radionuclide. The X-ray source 16 irradiates an object 19 to be imaged. The X-ray imaging device 14 is adapted to produce multiple frames 40 during at least part of the exposure/irradiation period. The mechanical manipulator 20 controls the movement of the X-ray source 16 and the imaging device 14 about at least one rotation axis along a spline, which may of course, be a circular or non-circular trajectory. The axis is located somewhere between the X-ray source focal point and the X-ray imaging device. The reconstruction algorithm 26 uses the multiple frames 40 to compose a panoramic image of a layer of the object under observation, the image having a focus depth which is different in at least some part of the panoramic image from the focus depth corresponding to a predetermined panoramic image.

The present invention is a scanning X-ray imaging system 10 wherein the X-ray source 16 is adapted for transmitting X-rays and exposing an object position to the x-rays. The object position 70 is a location that an object to be imaged is position for exposure to the X-rays, and is disposed between the X-ray source 16 and the X-ray imaging device 14. The combination of the X-ray source 16 and the imaging device 14 track along a path defined within the object position 70 over the course of an exposure cycle. This defined path corresponds to the pre-determined image layer speed profile. The scanning X-ray imaging device 14 is adapted for receiving transmitted X-rays and for producing multiple image frames during at least part of the exposure cycle. As the image frames 40 are produced, they are held/stored as corrected raw pixel signal data. If real time imaging is desired, the image frame data are held in a "fast" storage medium 17, otherwise they are held in another adequate storage medium.

Individual frames and groups of frames can be selectively recalled from the held/stored image frames 40. A selectable portion of the image frames 40 are selectable for use by a means that automatically reconstructs a focused tomographic image from two or more image layer speed profiles. An algorithm is used as the means that reconstructs a focused tomographic image. The user selects a region of interest (e.g., of the predetermined layer panoramic image) that it is desired to refocus. The algorithm accomplishes automatic refocusing by optimizing the image sharpness of the selected region of interest by doing a sharpness comparison between appropriate multiple frames with different speed profiles, which are otherwise analogous to the region of interest and replacing the region in the image with the sharper analogous region.

The digital imaging device has active area dimensions m×n, wherein m is the long dimension 530 and n is the short dimension 510 (see FIG. 6a) such that m/n>1.5 thus it has an elongated shape and is able to readout the frames 40 at 50 fps (frames per second) or more preferably 100 fps and even more preferably 300 fps or more. The m/n>1.5 geometry helps keep the costs of such a device down and indeed costs can be much less that a full field active area imaging device. This is particularly true where the imaging device is a CdTe-CMOS 560 or CdZnTe-CMOS imaging device.

Figure 13:
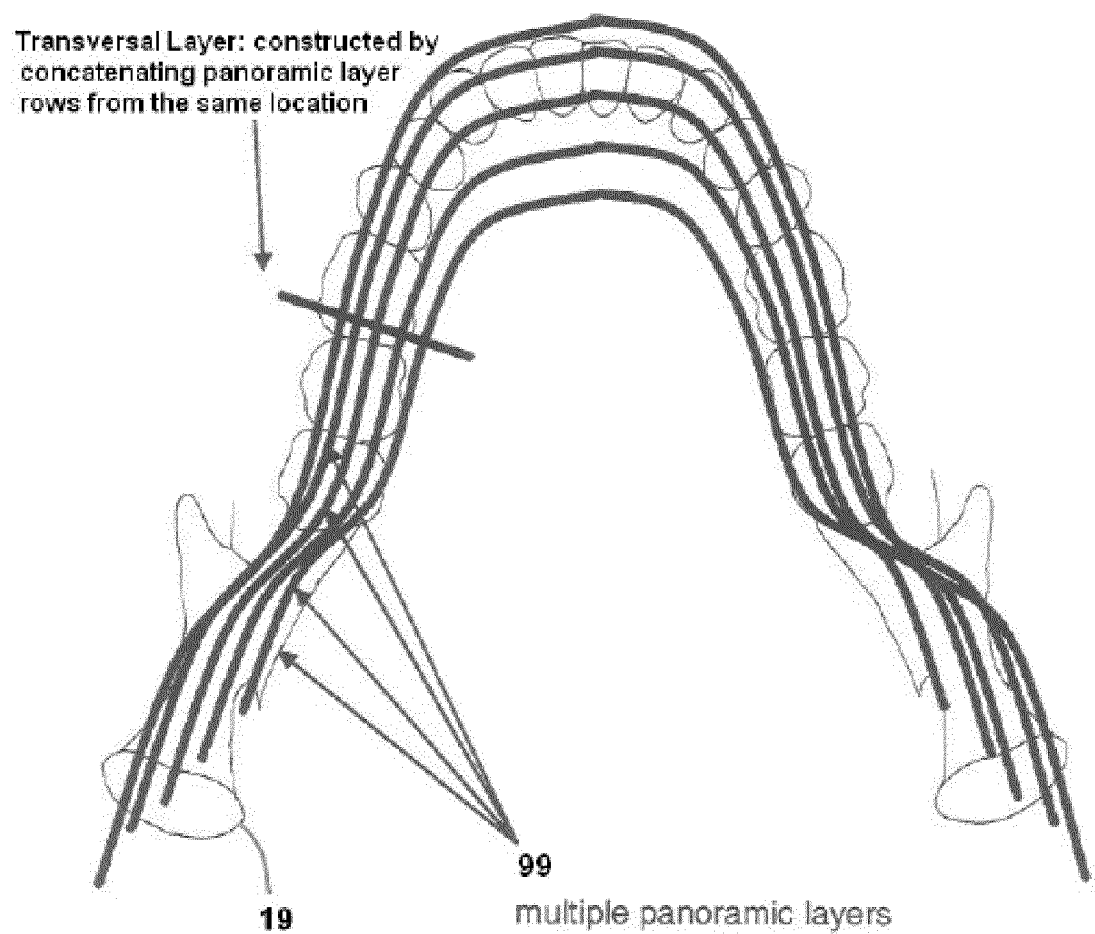
FIG. 13 is a top, schematic view of an example of a panoramic, transverse layer formed by concatenating rows from multiple panoramic images from the same location.

Furthermore, the mechanical manipulator's X-ray source arm 20 and digital imaging device 14 move in a continuous scan movement (not necessarily constant) for the duration of the useful part of the scan, i.e., the part of the scan that x-rays are emitted from the X-ray source 16 as needed to image substantially the whole jaw 19. The duration of the scan and the amount of x-rays emitted are comparable to the radiation dose required in a regular dental panoramic X-ray scan. The final images can be selected from a group of predetermined panoramic layer images 99 (see FIG. 13), other panoramic layers images (or at least part thereof 98), transverse slicing images, or 3-D images.

A real time storage device 17 such as RAM 18 (or a similarly fast data storage & access device) is used to store-and-hold all the frames 40 captured during an exposure. A digital processing unit 22 (for example, a typical computer CPU) is in electronic communication with the real time storage device 17 and executes the reconstruction algorithm using the frames 40 (corrected raw pixel array signal data) held on the storage device 17. The system 10 selectively produces dental panoramic X-ray images 12 or parts thereof, dental transverse X-ray images 224 and dental tomosynthetic 3D images from a frame stream produced by the high-speed, X-ray digital imaging device.

The imaging device 14 is a digital imaging device is a "frame mode" output device (as opposed to a "line" output device), outputting corrected raw frame data in frame mode output with a sufficient fast frame rate. This means that the imaging device is disposed to move substantially continuously relative to the object being scanned, and that the individually addressable imaging cell output values are readout at time intervals substantially corresponding to a point on the object image traversing between half and the full distance w of a detector pixel in the scanning direction during a scan. That is, that on average, frame shift intervals are more than half a pixel width (i.e., w/2=>0.5) in the direction of the scan, but less than a full pixel width s, averaged over all the frames in an exposure.

Figure 6A:
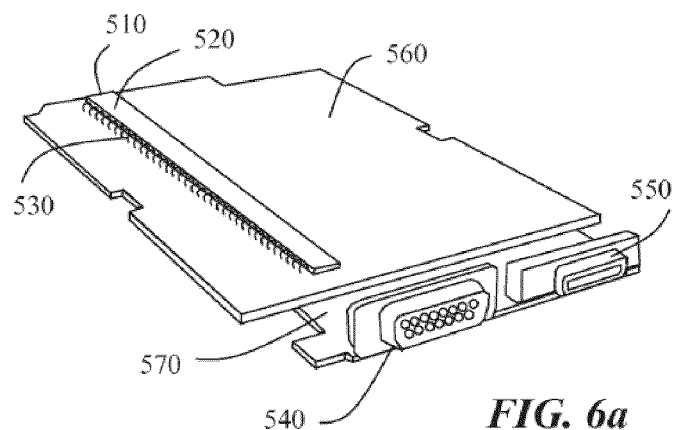
FIG. 6a is a drawn example of a high speed CdTe-CMOS X-ray digital imaging device in accordance with the invention that outputs many independent image frames.
Figure 6B:
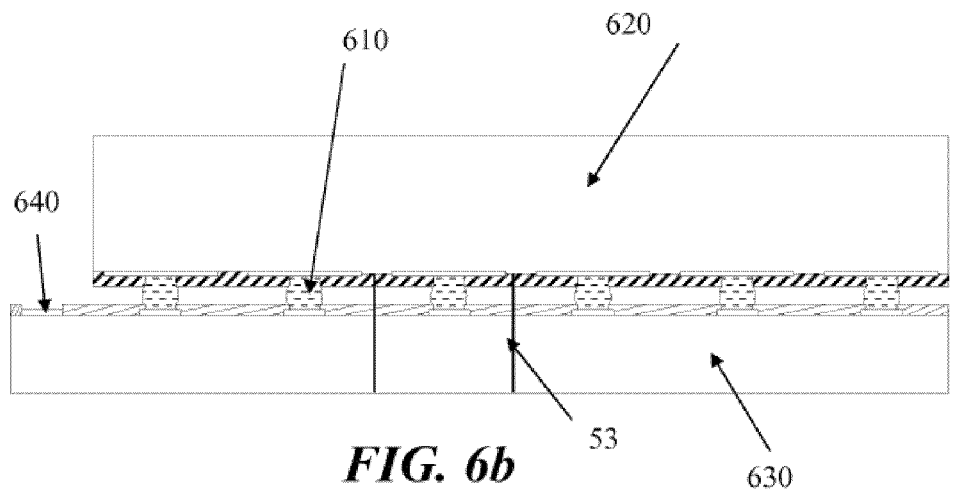
FIG. 6b is a schematic representation of a CdTe-CMOS hybrid which was used to construct the imaging device of FIG. 6a in accordance with the current invention.

A working embodiment of the present imaging device 14 is of the type shown in the photo in FIG. 6a. The elongated active area 520 of the imaging device comprised six CMOS/detector hybrids. FIG. 6b schematically illustrates such a CMOS/detector hybrid. The preferred detector substrate 620 illustrated comprised a Cadmium and Telluride composition, such as CdTe and CdZnTe, which absorbs the X-rays with extreme sensitivity and converts them directly to an electronic charge. The CMOS readout substrate 630 was in electrical communication with the detector substrate 620, by means of low temperature lead free solder bumps 610 (see U.S. Pat. No. 6,933,505). The individual CMOS/detector hybrids are connected electrically to the mother board 560 by means of wire bonding of pads 640 onto the corresponding pads of the mother board. Beneath the mother board 560 there is situated a readout or interface board 570 for controlling the mother board and producing a digital video signal which is readout via connector 550. Connector 550 can be of the camera link type protocol which is a commercially available readout protocol. Nevertheless, the readout can also happen through a variety of other readout protocols such as USB 2.0, firewire or gigabit Ethernet. The interface board also contains a power supply connector 540 which provides all the necessary supply voltages to the boards as well as High Voltage ("HV") to the CdTe detectors. A frame mode imaging device 14 in accordance with the invention produces independent image frames 40 by means of outputting sequentially or in random access, pixel values every so often and usually in predetermined time intervals.

Figure 5A:
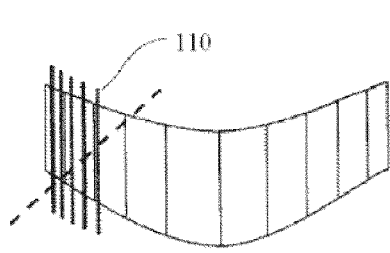
FIG. 5a is a schematic view of the readout and recording of an image using a prior art TDI-type device which records only a single layer by outputting image lines using the CCD TDI technique during the X-ray scan.

A frame 40 is understood to be a two dimensional spatial representation of pixel values 55, each pixel value 55 corresponding to the output from a physical pixel 53 in the imaging device or in some cases each pixel value 55 can correspond to a combination of output values from the imaging device physical pixels 53. The conversion of the output signal of an image device pixel 53 to its corresponding frame pixel value 55 can take place inside the imaging device or externally, for example inside the computer 22. The imaging device 14 is able to produce many individual frames 40 during the X-ray scan, with very high sensitivity. In a regular CCD based panoramic examination, the CCD works in the Time Delay Integration mode (TDI) which is well-known in the field. The output from a CCD imaging device is image lines 110 as depicted schematically in FIG. 5a. For the duration of the scan, the CCD outputs image lines 110 and at the end of the scan only one panoramic image layer 12 is reconstructed corresponding to a predetermined layer depending on the mechanical geometry of the panoramic unit and the speed profile and the positioning of the patient.

Figure 5B:
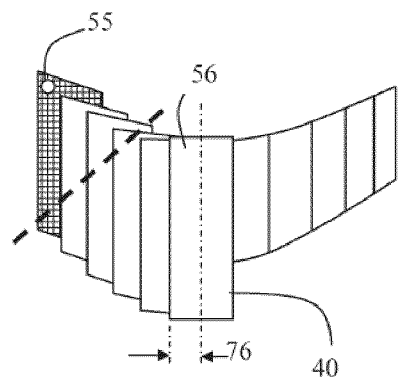
FIG. 5b is a schematic view of the readout in accordance with the present invention and recording of an image using a high-speed X-ray digital imaging device that outputs many independent overlapping frames.

On the other hand, the imaging device 14 of the type described in FIGS. 6a and 6b operates in frame output mode, with sufficient speed and excellent sensitivity to match the speed. The imaging device implemented by the applicant operates at frame rates of 50 fps to 300 fps or more depending on the mechanical scanning speed of the X-ray source. As shown in FIG. 5b, during the X-ray scan the output from the imaging device are frames 40 rather than lines, such frames 40 overlapping during the scan and providing the necessary data redundancy needed to reconstruct not only one but several dental panoramic layers, or parts of layers, transverse slicing and even 3-D tomosynthetic image reconstruction of teeth. The imaging device of FIG. 6a can also provide just raw independent pixel values and in this case, the frames 40 may be reconstructed then in the personal computer by rearranging the pixel values to frames.

The mechanical manipulator 20 has at least one rotation axis 34 located in a position other that the focal point 36 of the X-ray source. The alignment estimator 24 detects the camera position in 1D, 2D or 3D depending on the complexity of the trajectory. The panoramic reconstruction process 26 uses an algorithm to reconstruct the final images 12 out of the stored frames 40. The storage system 17 is capable of storing the frames 40 in real time in order to avoid frame loss and is therefore essentially a real time storage system such as RAM 18, or very fast hard drive or an drive array capable of transferring stored data at 10 MB/sec or faster and therefore able to store all the frames 40 captured during an exposure while permitting real time retrieval of such data. In a preferred embodiment, RAM 18 having a 50 MB/sec retrieval rate is a Kingston 400 MHz 2 GB DDR (model number KHX 3200AK2/2G). This RAM has a clock speed of 400 MHz and with every clock pulse it is able to store 8 bits. Models with RAM speeds of 5 GB/sec or more are available. These storage means may be located in the computer 22 or located in the imaging device 14 or at some other location. Storing frames 40 in real time here means with a time delay of not more than few seconds and preferably few milliseconds and even more preferably few microseconds. The processing unit 32 is a digital processing unit such as a personal computer 22, micro controller, FPGA or DSP, (not shown) capable of executing the reconstruction algorithm 26.

Figure 3:
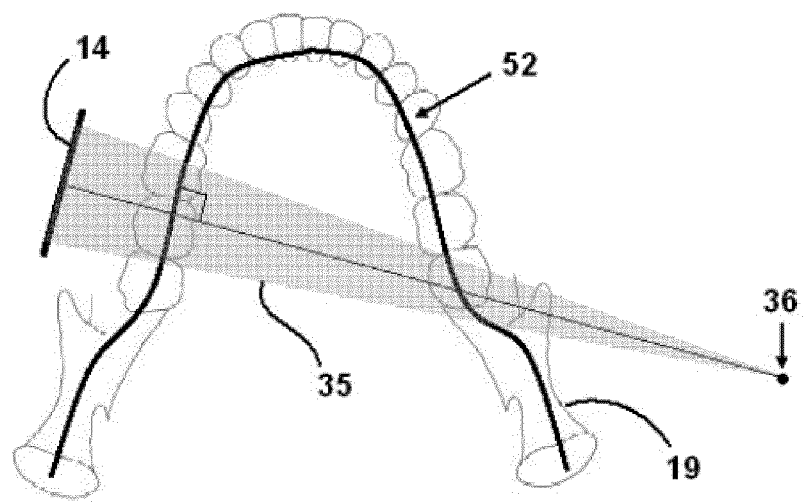
FIG. 3 is a schematic view of a lower jaw bone illustrating a panoramic layer-of-interest.
Figure 4:
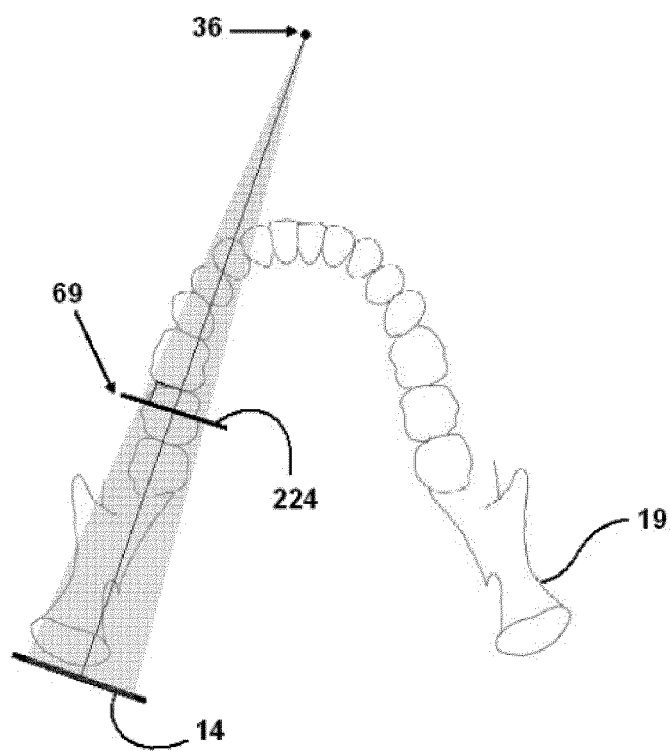
FIG. 4 is a schematic view of a lower jaw bone illustrating a transverse slice across a point on a panoramic layer-of-interest.

Referring now to FIGS. 3 and 4, the speed of the X-ray imaging device 14 combined with the reconstruction algorithm 26 allow formation of multiple dental X-ray images from the frames 40 of a single exposure. A single exposure refers here to a continuous measurement in which the whole layer-of-interest 52 (the layer-of-interest can be a part of the whole dental area) is exposed to radiation one or more times, but in which the apparent movement between two consecutive radiated frames 40 is never less than half the size of a pixel 53 and stays less than the full size w of the pixel 53. This results in there being ample overlap 56 between consecutive frames 40, but not at the expense of creating huge data sets that cannot be utilized in real time. This is particularly important in dental imaging where the user (dentist) is expecting to see an image 12 in effectively real-time and during the exposure.

Note that "Effectively Real-Time" as used herein means that the image 12 is displayed in less than 10 seconds after the end of the exposure and more preferably less than 5 seconds, and optimally, the image is displayed effectively simultaneously during the exposure. For this to be achieved, the frame rate or time intervals between consecutive frames 40 must not be shorter than what is needed to allow the physical pixels 53 to move by at least half a pixel width-size s, but short enough to have the detector pixels 53 move less than a full pixel width size s. Regarding such imaging devices 14 as were described herein with reference to FIGS. 6a and 6b, capable of producing multiple frame data with the above qualities, see WO2004055550 and EP 1520300.

The imaging device 14 and radiation source 16 of the present system 10 rotates around an axis 34 which is positioned between (but not necessarily crossing the volume of x-rays 35 from the source 16 to the imaging device 14) the X-ray source 16 and the imaging device 14. Furthermore, the frames 40 generated by the (CdTe-CMOS/CdZnTe-CMOS) imaging device 14 are temporarily stored in real time in a sufficiently large RAM 18, to allow real time processing and display of a dental panoramic image 12 of a layer 52. That is, a "reconstructed" or readable image begins to be presented (unfolds) for the viewer before the exposure cycle is fully completed. The processing of the frames 40 to produce such panoramic images 12 includes spatial (i.e. pixel) domain arithmetic.

Figure 7:
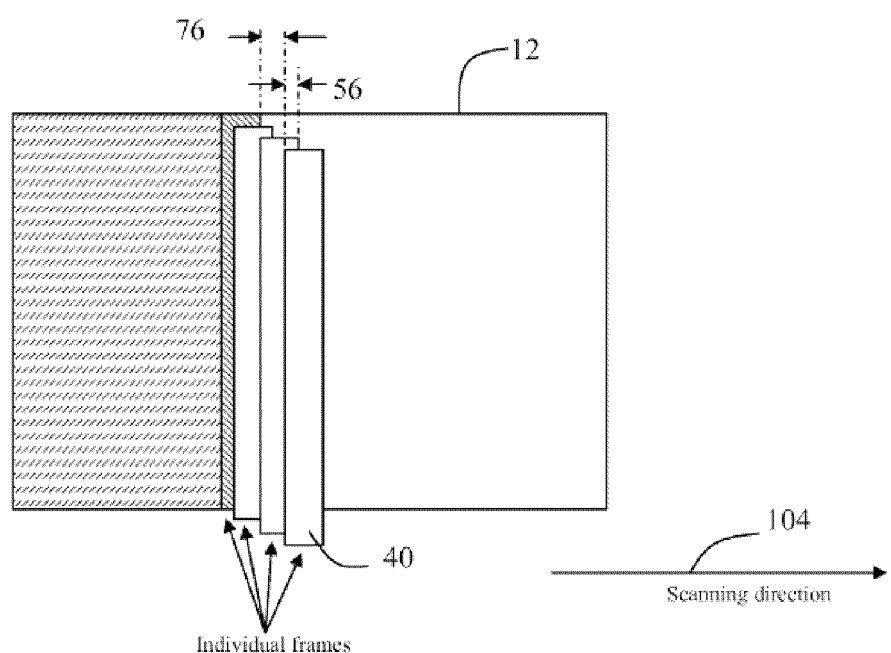
FIG. 7 is a schematic view of the reconstruction of an image in accordance with the present invention using the frames from the high-speed X-ray digital imaging device by means of >0.5<1 frame shift and addition of the individual frames.

The difference between a normal TDI-type device (not shown) and the present imaging system 10 is illustrated in FIGS. 5b and 7. A normal TDI-type device records only a single layer 12, while the present system 10 records multiple overlapping frames 40 which can be used to calculate multiple layers (both panoramic and transverse) and limited tomosynthetic 3D structures.

Referring now to FIGS. 6a and 6b, the imaging device 14 itself has an aperture 520 which is elongated (i.e., has one edge 530 which is much longer that the other edge 510). In this particular embodiment, one edge is 0.6 cm in width and the other is 15 cm in length. The device 14 has an active area made of an array of 1500.times.64 pixels. The detector active area 520 is made of six CMOS/detector hybrids and combined provides the active slot 520 which has two main dimensions: m and n where m is the long dimension 530 and n is the short dimension 510. As can be seen, m/n>>1. Preferably m/n>1.5, and even more preferably m/n>5 and even 10. In the embodiment disclosed in FIG. 6a, the ratio m/n was greater than 23. An important benefit of the preferred ratios achievable by the present system 10 is that: the larger the active area, the more expensive the detector is. For example, even with current mass produced flat panel TFT arrays, the price of an imaging device with m/n=1 or close to 1 is of the order $20,000 or even $30,000 USD. However, with an imaging device 14 of the present system 10, one is able to have the functionalities of regular panoramic equipment as well as at least partly, the functionality of the very expensive transverse slicing and 3-D reconstruction dental equipment.

The combination of the imaging device 14 and X-ray generator 16 rotate around the object position 70, i.e., the head of the patient 72, but the angular coverage can be less that a full circle as compared to a CT system (not shown). The position of the imaging device is either recorded as a one-dimensional position counter which tells the position of the current frame 40 in the final panoramic image 12, or it can record the full 3D position including orientation. The system 10 records the relative position of the imaging device 14 as a function of time, and thus it is possible to reconstruct a full dental image 12 from individual frames 40 stored. Referring again to FIG. 1, the simplest reconstruction is the one for producing a dental panoramic X-ray image 12. In this case, the position of the current frame 40 is recorded as a coordinate 74 in the final image 12. This coordinate 74 is then used to calculate the shift 76 required in a shift-and-add algorithm, mentioned above as the reconstruction algorithm 26 used in reconstructing the final image.

Referring again to FIGS. 8b and 8c, the sub-pixel shifting is accomplished by adding the pixels 55 in a frame 40 to two locations in the final image 12 multiplied by suitable weighting factors $w_{left}$, $w_{right}$. If the target position is x (non-integer or integer) and the position is increasing in a positive direction, then the pixel value 55 is added to positions floor(x) and ceil(x) where floor(x) refers to the largest integer smaller than x and ceil(x) refers smallest integer larger that x. The respective weighting coefficients $w_{left}$, $w_{right}$ are x-floor(x) and ceil (x)-x. The weighting factors $w_{left}$, $w_{right}$ can be global to a single frame 40, or can vary from pixel to pixel to compensate for any time delays between individual pixels. This is mathematically equivalent to interpolating the frames 40 and final image 12 linearly in the horizontal direction, shifting the frame pixels in the horizontal direction by an integer amount and then down-sampling the frames 40 and the final image to the original size. The sub-pixel shifting can also be implemented using any other interpolation method, for example with bi-linear, bi-cubic or spline interpolation. The sub-pixel shift-and-add algorithm 26 is implemented to eliminate extra jaggedness of diagonal edges compared to an integer shift-and-add algorithm (i.e., only use integer part of the position 86 without any interpolation or weighing).

Figure 9:
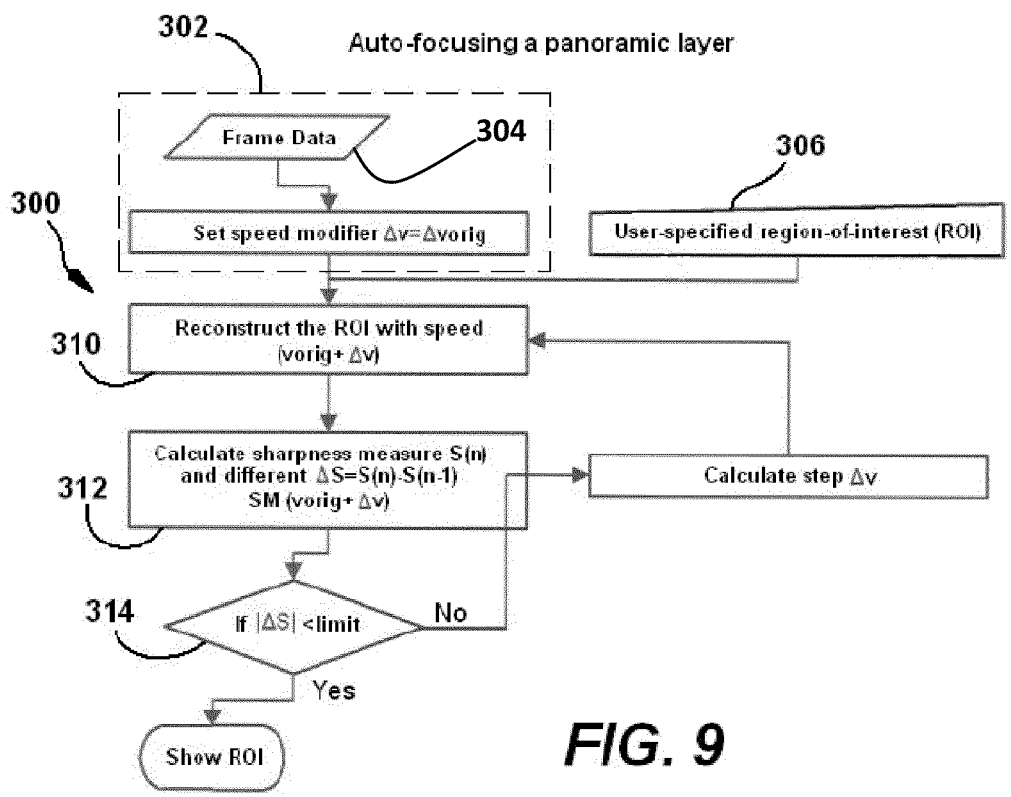
FIG. 9 is a flow chart of the auto-focusing feature of a panoramic layer in accordance with the invention.

Referring now to FIG. 9 an algorithm 300 is provided which auto-focuses a panoramic layer and automatically calculating the layer-of-best-focus for dental panoramic imaging. The algorithm 300 uses the multiple frames 40 to compose a panoramic image of a layer of the object under observation, the image having a focus depth which is different in at least some part of the panoramic image from the focus depth corresponding to a predetermined panoramic image. The algorithm 300 has five steps. In a first step 302, frame data 304 is used to reset the change in velocity $\Delta V$ of movement in the image plane compared to the change in original velocity $\Delta V_{orig}$. In a second step 306, the user specifies a region of interest. In a third step 310, the region of interest is reconstructed at the original speed $V_{orig}$ plus the change in velocity $\Delta V$. In a fourth step 312, the sharpness measure $S_{(n)}$ (sharpness measure S, which can either be a measure of contrast, roughness or some other measure of the image sharpness) and sharpness difference $\Delta S$ is calculated as being equal to $S_{(n)}$ minus $S_{(n-1)} \times SM(Vorig+\Delta V)$. In a fifth step 314, if $\Delta S$ is less than a particular limit, then the region of interest is displayed. Otherwise, calculate using a different step delta velocity $\Delta V$ and returns to step 310 and continue. The algorithm 300 can be applied globally to the whole final image 12 or locally to a given region-of-interest 98. Therefore, a user of the system 10 (e.g., a dentist) is able to observe and initial panoramic image 12 and then select a region (portion) 98 of the image 12 where blurring may be evident, in which case, the algorithm maximizes sharpness S of the selected part of the image. The result is a complete image 12 with all parts well in focus.

By reversing the direction in which the frames 40 are added to the final image 12, a completely different layer 60 can be reconstructed. By using the same speed profile 186, but reversed a direction, a mirror layer can be reconstructed. This mirror layer is on the opposite side of the patient, and in the dental panoramic imaging this equates to the area of the neck in the center part of the scan. So the invention provides a method to calculate the image of the spine. By re-projecting this image to the normal panoramic layer (by flipping the mirror image and applying suitable re-scaling function), an estimate of the blurring caused by the spine is obtained. This estimate can then be subtracted from the panoramic image 12 to decrease the effect of the spine on the image quality. As an end result, the panoramic image 12 is obtained without any potentially distracting superfluous images of the spine structure.

Example I

For typical a dental application of the present system 10, the elongated CMOS/detector sensor had an active slot 520 (FIG. 6a) of 150 mm×6.4 mm in size. The pixel size w in the scanning direction was typically 100 um, although smaller pixel sizes are achievable (but considered as unnecessary in dental extra-oral imaging). The exposure scan time was 5 to 30 seconds, with a frame rate of 200 to 300 fps (frames per second). The sensor moves about half a pixel size to less than one full pixel size w between consecutive frames 40. At that rate, the output frame data 304 can reach more than 750 MB for the entire scan which is a large data set, but still is quite manageable. It is essential therefore that the frame rate not be too high as this would not add anything to the image resolution and would only make data transfer and processing difficult, if not impossible, in real-time.

A video or frame grabber, based on a technology such as "CAMERALINK"™, was installed to a PCI Express slot of the PC 22 and used to capture frames 40. The frames 40 are then stored temporarily in RAM 18. This is very important, because otherwise it would be very difficult, if not impossible, to store and process 750 MB of data and display an image 12 that is reconstructed from such a large data set in real-time. In accordance with the present invention, the use of computer RAM 18 enables temporary storage of data.

Figure 8A:
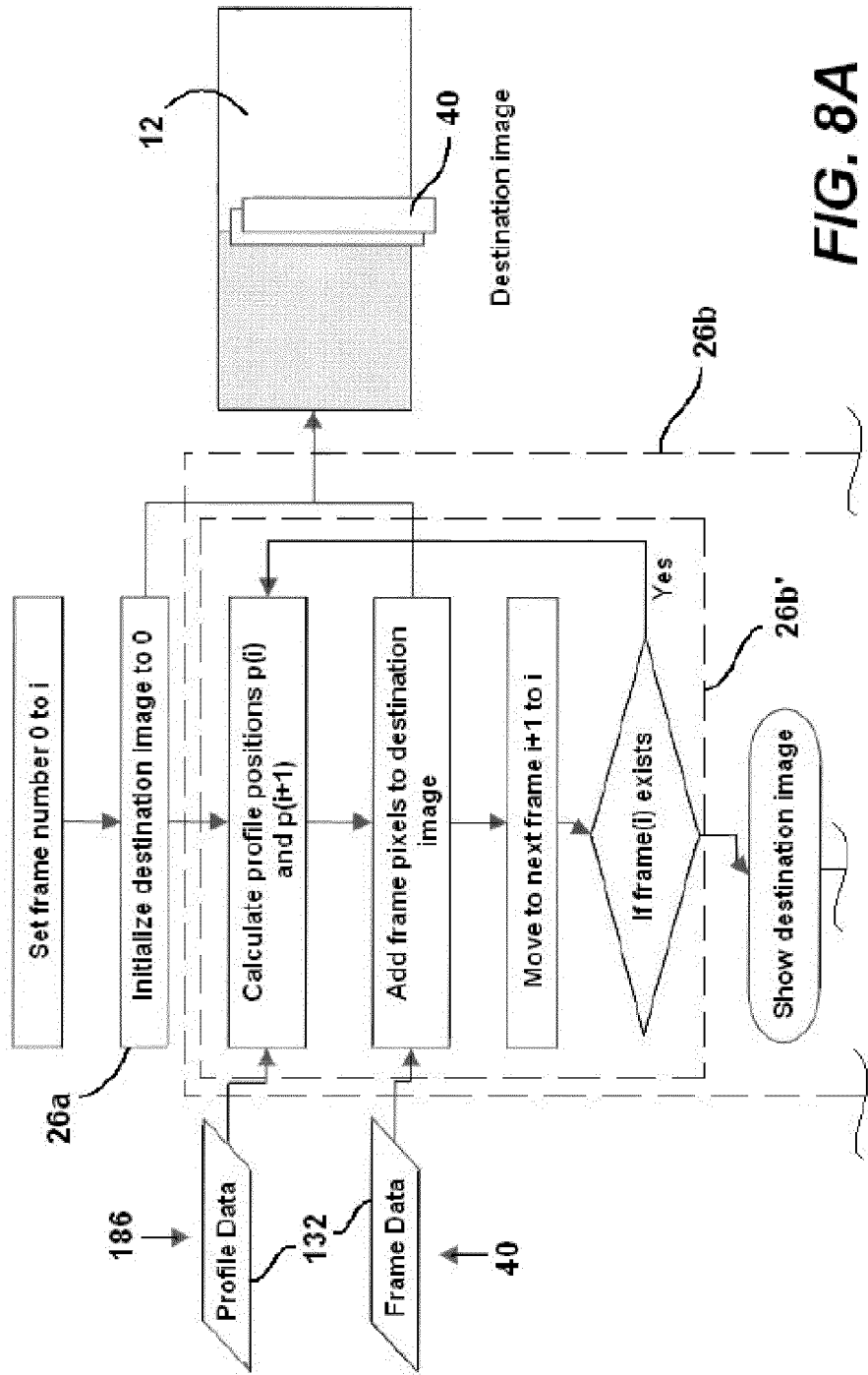
FIGS. 8a-b is a flow chart of the Time-compensated laminographic reconstruction (shift-and-add submethod) of the invention.
Figure 8B:
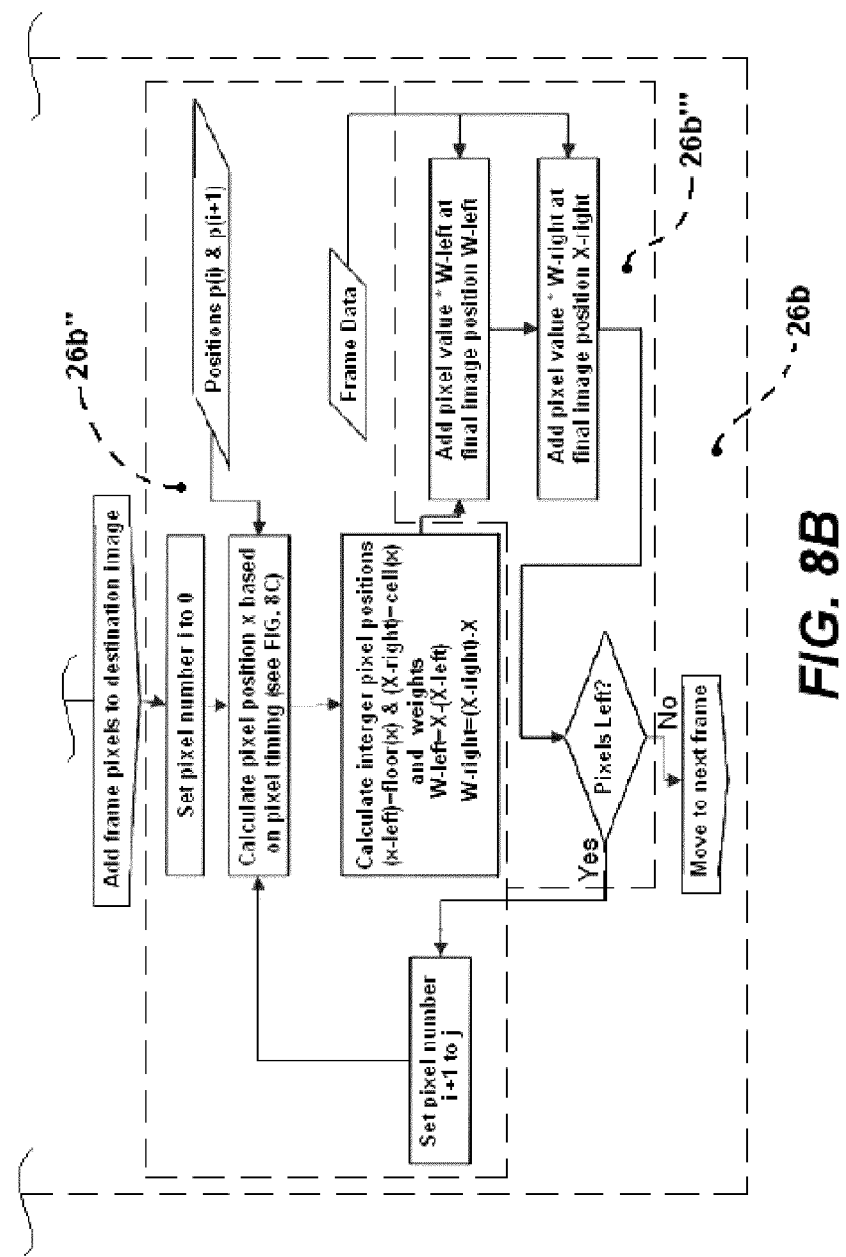
Figure 8C:
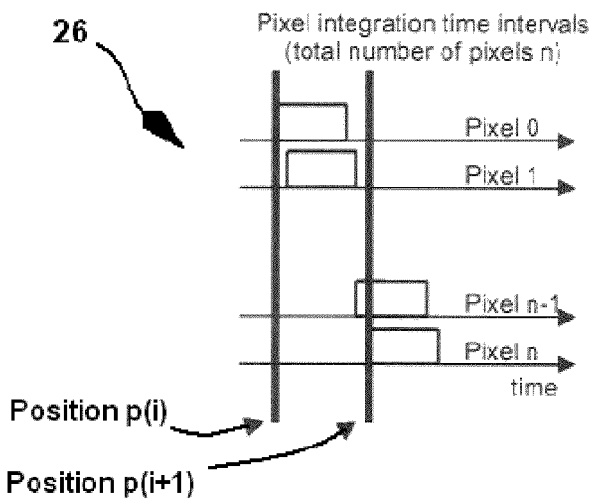
FIG. 8c is a schematic diagram of pixel signal value integration intervals over time.

Referring in particular to FIGS. 8a and 8b, the shift-and-add submethod of algorithm 26 is a fast processing method for reconstructing and displaying a panoramic layer 12 in real-time, and includes the following steps. In a first step 26a, the final image 12 is initialized with zero values. In a second step 26b, all the collected frames 40 are then processed one-by-one in the following manner: in a first substep 26b', for each frame pixel in an individual frame, the pixel position 86 is calculated. In a second substep 26b'', weighting coefficients are calculated according to FIG. 8b. In a third substep 26b''', the pixel value multiplied by the weighting factors is added to the pixel value of the final image 12 in locations specified in FIG. 8b.

Additionally, the system 10, can comprise a dedicated or separate processing device, for example incorporated within the imaging device 14, where the dedicated/separate processor runs the algorithm 26 or portion thereof for shifting and adding corresponding pixel values from at least two different frames to compose an image pixel in the panoramic image corresponding to a "virtual" speed profile different from the predetermined speed profile and a different (non-predetermined) layer. The speed profile relates to the speed at which the imaging device is actually scanning.

The present system 10 takes the frame data generated during a single exposure to selectively compose different types of images form the same frame data 40. Preferably, the system 10 composes at least two of a group of images selected from the group of reconstructable images consisting of: a predetermined dental panoramic layer image; an image comprising part of a non-predetermined dental panoramic layer image and the predetermined panoramic layer image; a transverse slice to a selected part of a dental panoramic layer image; and a 3-D reconstruction of a volume corresponding to some part of a dental panoramic layer. With this feature, a selectable part of the predetermined layer can be replaced with an analogous part of a different non-predetermined layer, to accomplish the re-focusing feature of the present invention. This how auto-focusing/manual focusing/re-focusing feature of the present system 10 is enabled.

After the display and processing, the data set 132 can be stored on a hard drive, a CD, a DVD and/or other non-volatile digital storage media. The use of RAM 18 to store the data temporarily and the fast reconstruction algorithm 26 mentioned above allows the image 12 to be reconstructed and displayed no later than seconds from the end of the exposure and usually within 5 seconds. In fact, the image 12 may be reconstructed from 750 MB of single frame data and displayed in real-time with a minimal delay (the delay needed for causality) during the actual exposure.

Example II

In another embodiment, the X-ray imaging device 14 produced multiple frames 40 during an exposure with time intervals during which the detector pixels were shifted by at least half a pixel length or more in the direction of scanning 104. Additionally, the detector pixels were shifted by at least half a pixel size, but less than the size w of a full pixel in the direction of scanning.

In accordance with another embodiment of the invention, all the individual frames 40 are stored temporarily in a RAM-type fast memory 18, and therefore it is possible to reconstruct the final image 12 with a modified position profile, after the actual exposure and after the initially displayed panoramic image 12. It is known of course, that the data can additionally be stored long term on a data storage system 22 such as a hard drive, CD or DVD and retrieved later back into fast memory. However, storing all the data on RAM 18 makes processing fast and efficient. Such is now possible because the amount of data needed to be stored has been significantly reduced given the amount of overlap between frames, and because of the elongated shape of the active area 520. Consequently, there is no need to wait for data to be downloaded, a process that normally takes several seconds. This, however, is not possible with TDI-type imaging devices, because the position synchronization has already been done in the camera hardware in analog domain, and thus cannot be modified.

The shifted amount 76 between consecutive frames 40 is normally determined from the position information gathered during the measurement. This should give a panoramic image 12 with the layer-of-interest 52 in full focus. Unfortunately, due to misalignment of the patient 72, or patient motion, different jaw profile or for many other reasons, there are very often portions in the panoramic image 12 that are out-of-focus or blurred. The shift 76 between consecutive frames 40 (i.e., the speed of the movement in the imaging plane 12) determines which layer 99 is well focused. If the movement speed of the camera 14 with respect to the X-ray source 16 is Vcamera, the distance between X-ray source focal point 36 and the imaging plane 12 is $d_1$, and the layer of interest 52 is at distance $d_2$ from the focal point 36, then the required speed $V_{shift}$ for the shift-and-add algorithm 26 is determined according to equation (1):

$$V_{shift}=(d_2/d_2)\times V\text{camera} \qquad (1).$$

Thus, by modifying the shifting amount 76, a different layer 99 can be focused. In theory; any layer 99 can be in focus, but the finite pixel size sets a limitation on how sharply a layer appears. If the shifting speed 76 is more than a pixel 53 per frame, the image resolution is degraded in the process. The shifting amount 76 can be modulated by software either globally or locally to allow either a completely different layer 99 to be displayed or to modify an existing layer to improve the sharpness in out-of-focus regions, which is usually the case in dental panoramic X-ray imaging.

The shift speed 76 cannot only be modified on a column-by-column basis. In addition, the speed 76 can vary on a row-by-row basis (i.e., every part of the image 12 might have a different speed). This enables bringing into focus of both upper 180 and lower teeth 182, for example, when the patient 19 has an incorrect bite (i.e., front and back teeth are not on the same vertical plane). This is an important feature of the present system 10, and can have tremendous impact on today's practice of dental radiology, because the blurred part of the image 12 can be brought into focus and displayed with the rest of the original panoramic image. Therefore, it is no longer necessary to re-expose the patient 19 a second, much less a third time. In this manner, the layer-of-interest 52 can be modified by altering the shifting amount 76 in the shift-and-add algorithm 26.

Figure 12:
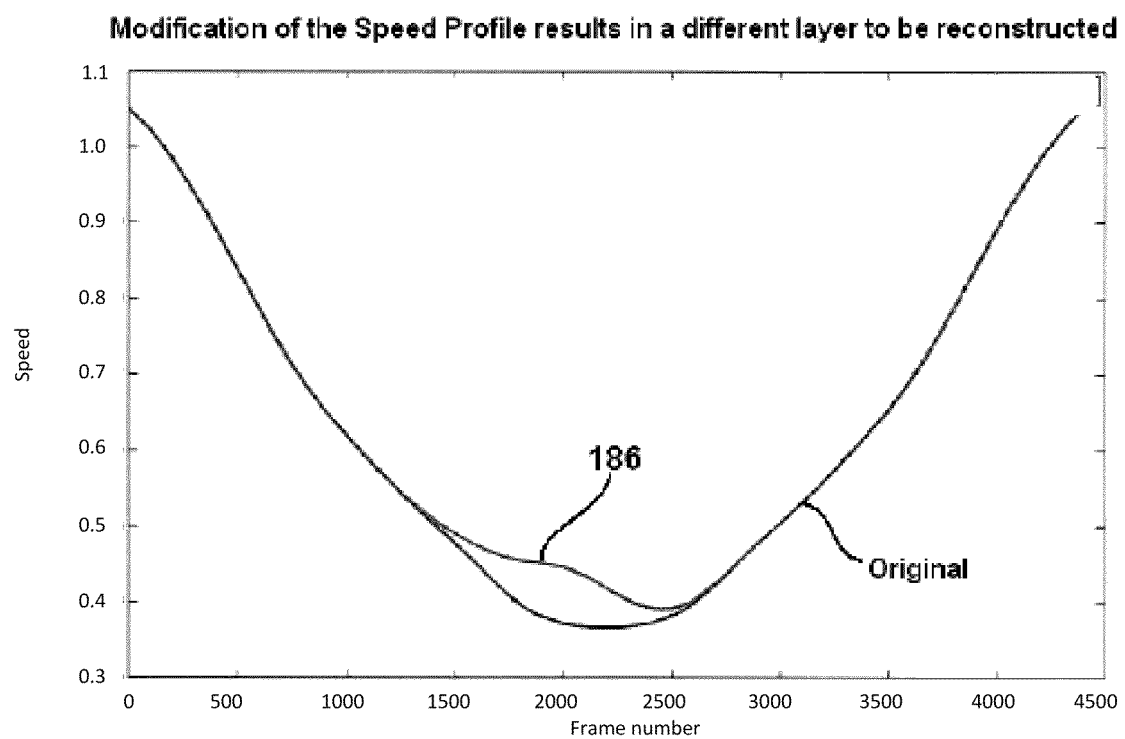
FIG. 12 is a graphical representation of the optimization of the speed profile.

In accordance with another embodiment of the present invention, the optimal speed profile 186 (see FIG. 12) may be calculated. Additionally, the present system 10 is adaptable to create panoramic dental images 12 which have a focus depth selectably different in some but not in all portions when compared to the focus depth of a predetermined panoramic image.

In still another embodiment, the system 10 is adapted to create panoramic dental images 12 in which the means of using multiple frames 40 comprises sub-pixel shifting and the adding of pixel values from different frames.

In another embodiment, the system 10 includes a means for creating a transverse dental image slice 224. This means uses multiple frames 40 to form the transverse image 224 by combining vertical pixel rows referring to the same physical transverse slice from multiple panoramic images.

Figure 10:
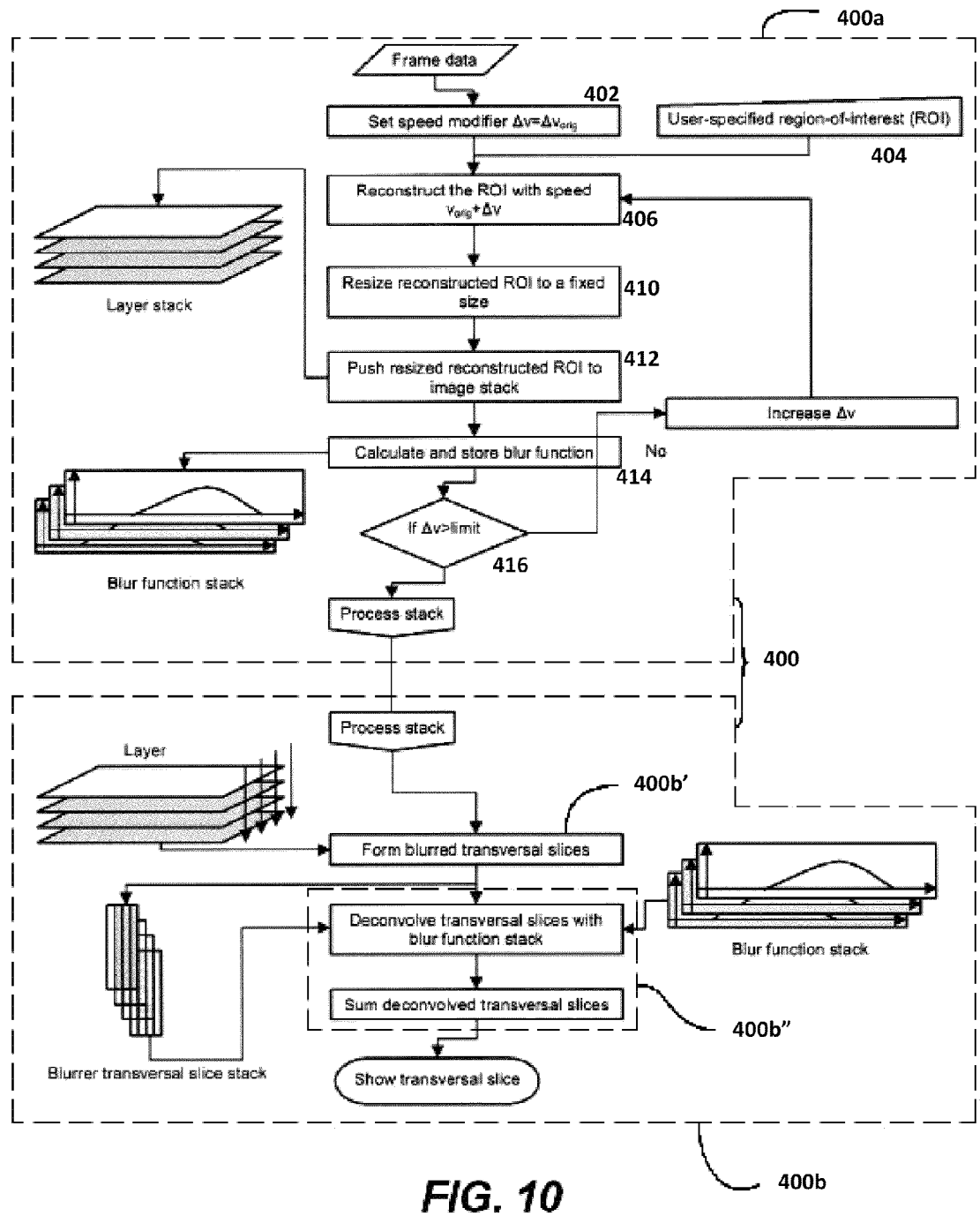
FIG. 10 is a flow chart of the feature of the present invention for calculating a transverse slice at a point on a panoramic layer.

Referring to FIG. 10, in another embodiment, the dental X-ray imaging system 10 of the invention includes an algorithm 400 which uses the multiple frames 40 to compose a transverse slice 224 with respect to a panoramic image. The algorithm 400 includes subroutines 400*a* and 400*b*. In the first subroutine 400*a*, in a first step 402, frame data 304 is used to reset the change in velocity $\Delta V$ to the original change in velocity $\Delta V$orig. In a second step 404, the user specifies a region of interest. In a third step 406, the region of interest is reconstructed at the original speed $\Delta V$orig plus the change in velocity LV. In a fourth step 410, the reconstructed region of interest is resized to a fixed size. In a fifth step 412, the resized reconstructed region of interest is pushed to the image layer stack. In a sixth step 414, a blur function is calculated and stored. In a seventh step 416, if delta velocity $\Delta V$ is greater than a particular limit, then the stack is processed in a transverse slice calculation subroutine 400*b*; otherwise, delta velocity $\Delta V$ is increased and the process returns to the third step 406 and continues. The transverse slice subroutine 400 thus forms a transverse image slice 224 in addition to a panoramic layer 60 using the frames 40 accumulated during the same exposure. In transverse imaging, the layer-of-interest 69 is perpendicular to a panoramic layer 52. Usually this is done as described earlier, but in accordance with this embodiment of the invention, this is performed more elegantly.

As described earlier, multiple panoramic layers can be calculated from a single measurement data set. By intelligently calculating correct speed modulation function, a transverse slice image 224 can be formed by concatenating the corresponding rows from individual panoramic layers in order of increasing depth. The algorithm 400*b* has the following steps: In a first step, method 400*b*' is applied to calculate multiple panoramic images, stored in a stack. In a second step 400*b*", the contribution of the 3D physical structure at different distances is calculated for every panoramic image 12. Every panoramic image 12 contains the image of the 3D physical model not only at the layer-of-interest, but also in front of and in back of it. This can be modeled using a blur function. In this step 400*b*''', the blurring is reversed using a de-convolution method, and thus the true image at different panoramic layers without crosstalk between neighboring layers is formed. The transverse image 224, formed by concatenating different panoramic layers 60, may now be displayed. Contrary to U.S. Pat. No. 6,496,557, which describes a system where the imaging plane is perpendicular or roughly perpendicular to the direction of radiation, the present invention discloses a system 10 which provides a layer 60 parallel (or close to parallel) to the direction of radiation.

Figure 11:
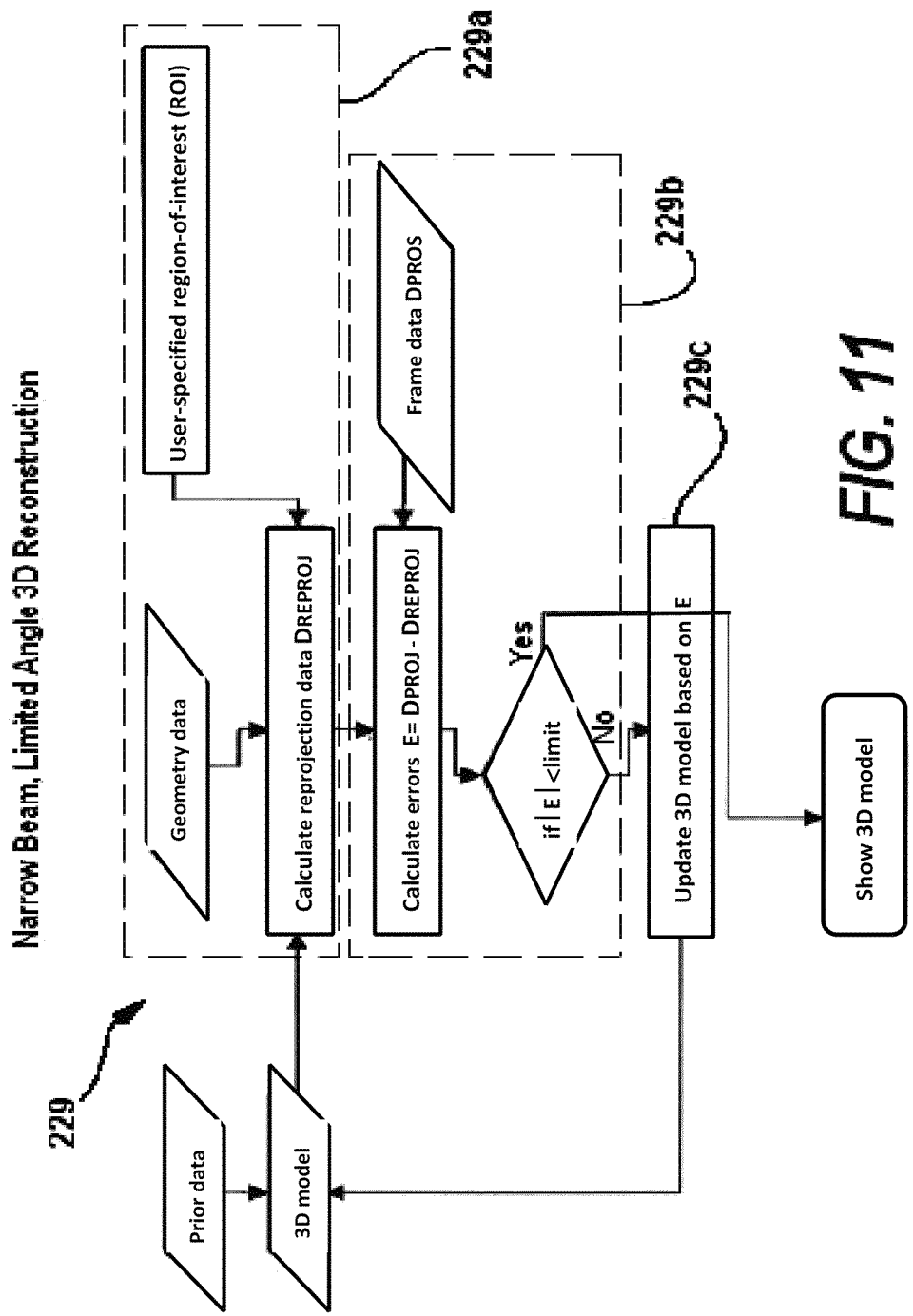
FIG. 11 is a flow chart of the feature of the present invention for calculating a 3-D image at point on a panoramic layer using a narrow beam, limited angle 3D reconstruction.

Referring now to FIG. 11, additionally, an imaging method 229 can be used to provide limited volumetric 3D images. The method 229 is an iterative algorithm, which, in step 229*a*, uses the geometry data (i.e., 3D location of X-ray source and the detector and the related movement profiles) to form re-projection data (i.e., estimates of the projected frames 40 based on the present 3D model). Then, in step 229*b*, the software calculates the error between measured and re-projected frames 40. In step 229*c*, this error is used to update the current 3D estimate. This operation is applied to a region-of-interest specified by the user. Because of the limited number of views, narrow projection rotational angles and narrow projection width, it is very important to use prior data in the reconstruction. Prior data is used to set restrictions on the 3D model, like smoothness, to produce and unique and meaningful result. The 3D image obtained is not comparable to full CT images in quality, but is sufficient for dental operations.

An object of the invention is to produce selectively predetermined dental panoramic image layers, dental panoramic X-ray images of different layers, dental transverse X-ray images and dental X-ray images from a frame stream produced by a high-speed, X-ray digital imaging device.

In an advantage, the system's 10 functioning on data from a single exposure spares the patient multiple exposures and allows for the first time effectively risk free exposures in dental radiology. Such system 10 has unique advantages and offers a breakthrough in the field of dental radiology.

In another advantage, the dentist is able with a single system 10 and single exposures to do examinations that previously required at least two if not more systems totaling a multiple in cost and a multiple of risk in patient diagnosis and treatment. Examinations become safer and less expensive for the patients who now only need take one exposure.

In another advantage, the system 10 applies little more radiation than the radiation dose used in a regular dental panoramic exposure and should employ X-ray scan mechanics that operate in continuous movement.

In another advantage, continuous movement means that the speed of scanning V is greater than zero at all times during the scan. The speed need not be constant.

In an advantage, CdTe or CdZnTe based digital imaging devices have an excellent sensitivity and absorb 95% of the incoming x-rays at dental application energies (i.e., from 10 kV up to 90 kV X-ray tube load).

In another advantage, the need for non-continuous, step-wise scans are eliminated, thus reducing the radiation doses and eliminating the longer step-wise scans, which create higher risk and discomfort to the patient. Because a continuous fast X-ray scan is possible, one does not need separate specialized dental equipment other than the normal panoramic X-ray units.

In another advantage, a system 10 and method are provided of combining data from a single exposure to not only reconstruct a panoramic layer of interest, but also to be able to correct part of the image that is blurred and furthermore produce transverse image slices and 3D images.

In another advantage, the system 10 and method of the invention produce a variety of formats of panoramic images from a high-speed, X-ray digital imaging device.

Multiple variations and modifications are possible in the embodiments of the invention described here. Although certain illustrative embodiments of the invention have been shown and described here, a wide range of modifications, changes, and substitutions is contemplated in the foregoing disclosure. In some instances, some features of the present invention may be employed without a corresponding use of the other features. Accordingly, it is appropriate that the foregoing description be construed broadly and understood as being given by way of illustration and example only, the spirit and scope of the invention being limited only by the appended claims.

GLOSSARY OF TERMS

CCD Charge coupled device: an imaging device capable of converting light to electric signals. In X-ray imaging, a CCD is usually coupled with a scintillator.

CT Computed tomography: a method of calculating full volumetric 3D data from multiple projections covering the full 360 degree rotational circle.

Imaging device: a device with multiple elements (pixels) able to convert X-ray radiation to a digital image.

Pixel column: a group of pixels perpendicular to a pixel row, i.e., pixels along a line perpendicular to the direction of movement.

Pixel row: a group of pixels in an imaging device in the movement direction. For example, if the camera is rotating around the vertical axis, a pixel row refers to pixels along a horizontal line.

Scintillator: a device able to convert X-ray radiation (for example x-rays and gamma) to light. A scintillator is usually coupled with a CCD to provide a device able to convert radiation to electric signals.

TDI Time-delayed Integration: a method in which a single scanned 2D image is formed by concatenating multiple lD line images.

A preferred embodiment of the invention provides a method for performing panoramic dental x-ray imaging comprising the steps of:

a. with an x-ray source, exposing x-rays to an object to be imaged by an x-ray imaging device suitable for producing multiple frames during at least part of the exposure;

b. around a rotational axis, rotating at least one of i) the x-ray source and ii) the imaging device, along a spline executing an exposure profile and during at least part of said exposure profile, x-rays are emitted by the x-ray source, the axis being located between a focal point of the x-ray source and the x-ray imaging device, wherein the x-ray imaging device has an active area with a long dimension (m) and a short dimension (n), a ratio of the long dimension to the short dimension being at least 1.5 (m/n>1.5);

c. storing the collected and irradiated frames, with a time delay of not more than one second, in a real time storage and retrieval system; and d. with a reconstruction algorithm, reconstructing and displaying a panoramic layer from the stored and retrieved irradiated frames, said panoramic layer being displayed no later than 10 seconds from the end of said exposure profile.

Another preferred embodiment of the invention provides method for performing dental extra-oral x-ray imaging comprising the steps of:

a. providing an x-ray source exposing x-rays to an object to be imaged;

b. providing an x-ray imaging device suitable for producing multiple frames during at least part of the exposure;

c. providing at least one rotational axis around which axis at least one of i) the x-ray source and ii) the imaging device rotates along a spline executing an exposure profile and during at least part of said exposure profile, x-rays are emitted by said x-ray source, the axis being located between a focal point of the x-ray source and the x-ray imaging device, wherein the x-ray imaging device has an active area with a long dimension (m) and a short dimension (n), a ratio of the long dimension to the short dimension being at least 1.5 (m/n>1.5);

d. using at least some of the frames collected during said exposure profile with at least one algorithm to reconstruct at least two of:

d1. a first panoramic layer, the first panoramic layer being a default panoramic layer, d2. a second panoramic layer comprised of at least one of a panoramic layer and ii) a part of a panoramic layer, positioned in a pre-determined position in the space available between the x-ray source and x-ray imaging device, said second panoramic layer being different, at least in part, from said default panoramic layer, d3. a third panoramic layer comprised of at least one more panoramic layer positioned in a user-selected position in a space available between the x-ray source and x-ray imaging device, said third layer being different, at least in part, from said default panoramic layer, d4. a fourth panoramic layer comprised of a panoramic layer adjusted manually by a user in a region of interest to have a different focal depth from the default panoramic layer in the region of interest, d5. a transverse slice to a region of interest in one of the first, second, third, and fourth panoramic layers, d6. a three-dimensional (3D) image of a region of interest in one of the first, second, third, and fourth panoramic layers, and d7. a partial panoramic layer corresponding to a region of interest and positioned in a selected space location available between the x-ray source and x-ray imaging device.

What is claimed is:

1. A system for performing panoramic dental x-ray imaging, comprising:

an x-ray source configured for exposing an object to be imaged to x-rays;

an x-ray imaging device configured for producing multiple frames during at least part of the exposure; and a manipulator providing at least one rotational axis around which axis at least one of i) the x-ray source and ii) the imaging device, rotates along a spline executing an exposure profile and during at least part of said exposure profile, x-rays are emitted by said x-ray source, the axis being located between a focal point of the x-ray source and the x-ray imaging device, wherein the x-ray imaging device has an active area with a long dimension (m) and a short dimension (n), a ratio of the long dimension to the short dimension being at least 1.5 (m/n>1.5);

a real time storage and real time retrieval system for storing and accessing in a non-destructive manner, generated and irradiated frames, received from the x-ray imaging device, with a time delay of not more than one second from the time each frame was produced by the x-ray imaging device; and a processing unit operating a reconstruction algorithm for reconstructing a panoramic layer from the stored and retrieved irradiated frames and displaying said panoramic layer no later than 10 seconds from the end of said exposure profile.

2. A system for performing dental extra-oral x-ray imaging, comprising:

an x-ray source configured for exposing an object to be imaged to x-rays;

an x-ray imaging device configured for producing multiple frames during at least part of the exposure;

a manipulator providing at least one rotational axis around which axis at least one of i) the x-ray source and ii) the imaging device rotates along a spline executing an exposure profile and during at least part of said exposure profile, x-rays are emitted by said x-ray source, the axis being located between a focal point of the x-ray source and the x-ray imaging device, wherein the x-ray imaging device has an active area with a long dimension (m) and a short dimension (n), a ratio of the long dimension to the short dimension being at least 1.5 (m/n>1.5);

a processing unit operating to access in a non-destructive manner and use at least some of the frames collected during said exposure profile with at least one algorithm to reconstruct at least two of:
- a first panoramic layer, the first panoramic layer being a default panoramic layer,
- a second panoramic layer comprised of a part of a panoramic layer, positioned in a pre-determined position in the space available between the x-ray source and x-ray imaging device, said second panoramic layer being different, at least in part, from said default panoramic layer,
- a third panoramic layer comprised of at least one more panoramic layer positioned in a user-selected position in a space available between the x-ray source and x-ray imaging device, said third layer being different, at least in part, from said default panoramic layer,
- a fourth panoramic layer comprised of a panoramic layer adjusted manually by a user in a region of interest to have a different focal depth from the default panoramic layer in the region of interest, and
- a partial panoramic layer corresponding to a region of interest and positioned in a selected space location available between the x-ray source and x-ray imaging device.

3. A system for performing panoramic dental x-ray imaging, comprising:
- an x-ray source, exposing an object to be imaged to x-rays by an x-ray imaging device suitable for producing multiple frames during at least part of the exposure;
- a manipulator providing a rotational axis, and around a rotational axis, rotating at least one of i) the x-ray source and ii) the imaging device, along a spline executing an exposure profile and during at least part of said exposure profile, x-rays are emitted by the x-ray source, the axis being located between a focal point of the x-ray source and the x-ray imaging device, wherein the x-ray imaging device has an active area with a long dimension (m) and a short dimension (n), a ratio of the long dimension to the short dimension being at least 1.5 (m/n>1.5);
- a real time storage and real time retrieval system storing and accessing in a non-destructive manner, generated and irradiated frames, received from the x-ray imaging device, with a time delay of not more than one second from the time each frame was produced by the x-ray imaging device; and
- a processing unit operating a reconstruction algorithm, reconstructing and displaying a panoramic layer from the stored and retrieved irradiated frames, said panoramic layer being displayed no later than 10 seconds from the end of said exposure profile.

4. A method, utilizing the system of claim 1, for performing panoramic dental x-ray imaging, the method comprising the steps of:
a. exposing the object to be imaged to x-rays;
b. producing multiple frames during at least part of the exposure; and
c. providing at least one rotational axis around which axis at least one of i) the x-ray source and ii) the imaging device, rotates along a spline executing an exposure profile and during at least part of said exposure profile, x-rays are emitted by said x-ray source, the axis being located between a focal point of the x-ray source and the x-ray imaging device, wherein the x-ray imaging device has an active area with a long dimension (m) and a short dimension (n), a ratio of the long dimension to the short dimension being at least 1.5 (m/n>1.5);
d. providing a real time storage and retrieval of the stored irradiated frames with a time delay of not more than one second; and
e. utilizing the reconstruction algorithm for reconstructing a panoramic layer from the stored and retrieved irradiated frames and displaying said panoramic layer no later than 10 seconds from the end of said exposure profile.

5. A method, utilizing the system of claim 2, for performing dental extra-oral x-ray imaging, the method comprising the steps of:
a. exposing the object to be imaged to x-rays;
b. producing multiple frames during at least part of the exposure;
c. providing at least one rotational axis around which axis at least one of i) the x-ray source and ii) the imaging device rotates along a spline executing an exposure profile and during at least part of said exposure profile, x-rays are emitted by said x-ray source, the axis being located between a focal point of the x-ray source and the x-ray imaging device, wherein the x-ray imaging device has an active area with a long dimension (m) and a short dimension (n), a ratio of the long dimension to the short dimension being at least 1.5 (m/n>1.5);
d. using at least some of the frames collected during said exposure profile with at least one algorithm to reconstruct at least two of:
  d1. a first panoramic layer, the first panoramic layer being a default panoramic layer,
  d2. a second panoramic layer comprised of at least one of i) a panoramic layer and ii) a part of a panoramic layer, positioned in a pre-determined position in the space available between the x-ray source and x-ray imaging device, said second panoramic layer being different, at least in part, from said default panoramic layer,
  d3. a third panoramic layer comprised of at least one more panoramic layer positioned in a user-selected position in a space available between the x-ray source and x-ray imaging device, said third layer being different, at least in part, from said default panoramic layer,
  d4. a fourth panoramic layer comprised of a panoramic layer adjusted manually by a user in a region of interest to have a different focal depth from the default panoramic layer in the region of interest,
  d5. a partial panoramic layer corresponding to a region of interest and positioned in a selected space location available between the x-ray source and x-ray imaging device.

6. A method, utilizing the system of claim 3, for performing panoramic dental x-ray imaging, the method comprising the steps of:
a. with the x-ray source, exposing an object to be imaged to x-rays by an x-ray imaging device suitable for producing multiple frames during at least part of the exposure;
b. around the rotational axis, rotating at least one of i) the x-ray source and ii) the imaging device, along a spline executing an exposure profile and during at least part of said exposure profile, x-rays are emitted by the x-ray source, the axis being located between a focal point of the x-ray source and the x-ray imaging device, wherein the x-ray imaging device has an active area with a long dimension (m) and a short dimension (n), a ratio of the long dimension to the short dimension being at least 1.5 (m/n>1.5);
c. storing the collected and irradiated frames, with a time delay of not more than one second, in a real time storage and retrieval system; and
d. with a reconstruction algorithm, reconstructing and displaying a panoramic layer from the stored and retrieved irradiated frames, said panoramic layer being displayed no later than 10 seconds from the end of said exposure profile.

7. A method, utilizing the system of claim 2, for performing dental extra-oral x-ray imaging, the method comprising the steps of:
a. exposing the object to be imaged to x-rays;
b. producing multiple frames during at least part of the exposure;
c. providing at least one rotational axis around which axis at least one of i) the x-ray source and ii) the imaging device rotates along a spline executing an exposure profile and during at least part of said exposure profile, x-rays are emitted by said x-ray source, the axis being located between a focal point of the x-ray source and the x-ray imaging device, wherein the x-ray imaging device has an active area with a long dimension (m) and a short dimension (n), a ratio of the long dimension to the short dimension being at least 1.5 (m/n>1.5);
d. using at least some of the frames collected during said exposure profile with at least one algorithm to reconstruct at least two of:
d1. a first panoramic layer, the first panoramic layer being a default panoramic layer,
d2. a second panoramic layer comprised of at least one of i) a panoramic layer and ii) a part of a panoramic layer, positioned in a pre-determined position in the space available between the x-ray source and x-ray imaging device, said second panoramic layer being different, at least in part, from said default panoramic layer,
d3. a third panoramic layer comprised of at least one more panoramic layer positioned in a user-selected position in a space available between the x-ray source and x-ray imaging device, said third layer being different, at least in part, from said default panoramic layer, and
d4. a fourth panoramic layer comprised of a panoramic layer adjusted manually by a user in a region of interest to have a different focal depth from the default panoramic layer in the region of interest.

8. A method, utilizing the system of claim 5, for performing dental extra-oral x-ray imaging, the method comprising the steps of:
a. exposing the object to be imaged to x-rays;
b. producing multiple frames during at least part of the exposure;
c. providing at least one rotational axis around which axis at least one of i) the x-ray source and ii) the imaging device rotates along a spline executing an exposure profile and during at least part of said exposure profile, x-rays are emitted by said x-ray source, the axis being located between a focal point of the x-ray source and the x-ray imaging device, wherein the x-ray imaging device has an active area with a long dimension (m) and a short dimension (n), a ratio of the long dimension to the short dimension being at least 1.5 (m/n>1.5);
d. using at least some of the frames collected during said exposure profile with at least one algorithm to reconstruct at least:
d1. a first panoramic layer, the first panoramic layer being a default panoramic layer, and
d2. a second panoramic layer comprised of at least one of i) a panoramic layer and ii) a part of a panoramic layer, positioned in a pre-determined position in the space available between the x-ray source and x-ray imaging device, said second panoramic layer being different, at least in part, from said default panoramic layer.

9. A method, utilizing the system of claim 2, for performing dental extra-oral x-ray imaging, the method comprising the steps of:
a. exposing the object to be imaged to x-rays;
b. producing multiple frames during at least part of the exposure;
c. providing at least one rotational axis around which axis at least one of i) the x-ray source and ii) the imaging device rotates along a spline executing an exposure profile and during at least part of said exposure profile, x-rays are emitted by said x-ray source, the axis being located between a focal point of the x-ray source and the x-ray imaging device, wherein the x-ray imaging device has an active area with a long dimension (m) and a short dimension (n), a ratio of the long dimension to the short dimension being at least 1.5 (m/n>1.5);
d. using at least some of the frames collected during said exposure profile with at least one algorithm to reconstruct at least:
d1. a first panoramic layer, the first panoramic layer being a default panoramic layer, and
d3. a third panoramic layer comprised of at least one more panoramic layer positioned in a user-selected position in a space available between the x-ray source and x-ray imaging device, said third layer being different, at least in part, from said default panoramic layer.

10. A method, utilizing the system of claim 2, for performing dental extra-oral x-ray imaging, the method comprising the steps of:
a. exposing the object to be imaged to x-rays;
b. producing multiple frames during at least part of the exposure;
c. providing at least one rotational axis around which axis at least one of i) the x-ray source and ii) the imaging device rotates along a spline executing an exposure profile and during at least part of said exposure profile, x-rays are emitted by said x-ray source, the axis being located between a focal point of the x-ray source and the x-ray imaging device, wherein the x-ray imaging device has an active area with a long dimension (m) and a short dimension (n), a ratio of the long dimension to the short dimension being at least 1.5 (m/n>1.5);
d. using at least some of the frames collected during said exposure profile with at least one algorithm to reconstruct at least:
d1. a first panoramic layer, the first panoramic layer being a default panoramic layer, and
d4. a fourth panoramic layer comprised of a panoramic layer adjusted manually by a user in a region of interest to have a different focal depth from the default panoramic layer in the region of interest.

11. A method, utilizing the system of claim 5, for performing dental extra-oral x-ray imaging, the method comprising the steps of:
a. exposing the object to be imaged to x-rays;
b. producing multiple frames during at least part of the exposure;
c. providing at least one rotational axis around which axis at least one of i) the x-ray source and ii) the imaging device rotates along a spline executing an exposure profile and during at least part of said exposure profile, x-rays are emitted by said x-ray source, the axis being located between a focal point of the x-ray source and the x-ray imaging device, wherein the x-ray imaging device has an active area with a long dimension (m) and a short dimension (n), a ratio of the long dimension to the short dimension being at least 1.5 (m/n>1.5);

d. using at least some of the frames collected during said exposure profile with at least one algorithm to reconstruct at least:
d1. a first panoramic layer, the first panoramic layer being a default panoramic layer, and
d5. a partial panoramic layer corresponding to a region of interest and positioned in a selected space location available between the x-ray source and x-ray imaging device.

12. A method, utilizing the system of claim 4, for performing panoramic dental x-ray imaging, the method comprising the steps of:
a. exposing the object to be imaged to x-rays;
b. producing multiple frames during at least part of the exposure; and
c. providing at least one rotational axis around which axis at least one of i) the x-ray source and ii) the imaging device, rotates along a spline executing an exposure profile and during at least part of said exposure profile, x-rays are emitted by said x-ray source, the axis being located between a focal point of the x-ray source and the x-ray imaging device, wherein the x-ray imaging device has an active area with a long dimension (m) and a short dimension (n), a ratio of the long dimension to the short dimension being at least 1.5 (m/n>1.5);
d. providing a real time non-volatile storage and retrieval of the stored irradiated frames with a time delay of not more than one second; and
e. utilizing the reconstruction algorithm for reconstructing a panoramic layer from the stored and retrieved irradiated frames and displaying said panoramic layer no later than 10 seconds from the end of said exposure profile, the stored irradiated frames remaining in the a real time storage and real time retrieval system at least until said panoramic layer is displayed.

13. A method, utilizing the system of claim 1, for performing panoramic dental x-ray imaging, the method comprising the steps of:
a. exposing the object to be imaged to x-rays;
b. producing multiple frames during at least part of the exposure; and
c. providing at least one rotational axis around which axis at least one of i) the x-ray source and ii) the imaging device, rotates along a spline executing an exposure profile and during at least part of said exposure profile, x-rays are emitted by said x-ray source, the axis being located between a focal point of the x-ray source and the x-ray imaging device, wherein the x-ray imaging device has an active area with a long dimension (m) and a short dimension (n), a ratio of the long dimension to the short dimension being at least 1.5 (m/n>1.5);
d. providing a real time storage and retrieval of the stored irradiated frames with a time delay of not more than one second;
e. utilizing the reconstruction algorithm for reconstructing a panoramic layer from the stored and retrieved irradiated frames and displaying said panoramic layer no later than 10 seconds from the end of said exposure profile; and
f. after reconstructing the panoramic layer from the stored and retrieved irradiated frames, storing the stored irradiated frames of the real time storage and real time retrieval system to a non-volatile digital storage medium.

14. A method, utilizing the system of claim 4, for performing panoramic dental x-ray imaging, the method comprising the steps of:
a. exposing the object to be imaged to x-rays;
b. producing multiple frames during at least part of the exposure; and
c. providing at least one rotational axis around which axis at least one of i) the x-ray source and ii) the imaging device, rotates along a spline executing an exposure profile and during at least part of said exposure profile, x-rays are emitted by said x-ray source, the axis being located between a focal point of the x-ray source and the x-ray imaging device, wherein the x-ray imaging device has an active area with a long dimension (m) and a short dimension (n), a ratio of the long dimension to the short dimension being at least 1.5 (m/n>1.5);
d. providing a real time storage and retrieval of the stored irradiated frames with a time delay of not more than one second in an non-volatile digital storage medium; and
e. utilizing the reconstruction algorithm for reconstructing a panoramic layer from the stored and retrieved irradiated frames and displaying said panoramic layer no later than 10 seconds from the end of said exposure profile.

15. A method, utilizing the system of claim 1, for performing panoramic dental x-ray imaging, the method comprising the steps of:
a. exposing the object to be imaged to x-rays;
b. producing multiple frames during at least part of the exposure; and
c. providing at least one rotational axis around which axis at least one of i) the x-ray source and ii) the imaging device, rotates along a spline executing an exposure profile and during at least part of said exposure profile, x-rays are emitted by said x-ray source, the axis being located between a focal point of the x-ray source and the x-ray imaging device, wherein the x-ray imaging device has an active area with a long dimension (m) and a short dimension (n), a ratio of the long dimension to the short dimension being at least 1.5 (m/n>1.5);
d. providing a real time storage and retrieval of the stored irradiated frames with a time delay of not more than one second;
e. utilizing the reconstruction algorithm for reconstructing a panoramic layer from the stored and retrieved irradiated frames and displaying said panoramic layer no later than 10 seconds from the end of said exposure profile;
f. after reconstructing the panoramic layer from the stored and retrieved irradiated frames, storing the stored irradiated frames of the real time storage and real time retrieval system to a non-volatile digital storage medium; and
g. utilizing the reconstruction algorithm for reconstructing another panoramic layer from the irradiated frames stored in the non-volatile digital storage medium, and displaying said panoramic layer no later than 10 seconds from the end of said exposure profile.

* * * * *